United States Patent
Lelyveld et al.

(10) Patent No.: US 12,428,658 B2
(45) Date of Patent: Sep. 30, 2025

(54) METHODS AND COMPOSITIONS FOR ENZYMATIC POLYMERIZATION OF N3'→P5' PHOSPHORAMIDATE DNA

(71) Applicant: The General Hospital Corporation, Boston, MA (US)

(72) Inventors: Victor Lelyveld, Lexington, MA (US); Jack Szostak, Boston, MA (US); Wen Zhang, Hopkinton, MA (US)

(73) Assignee: The General Hospital Corporation, Boston, MA (US)

( * ) Notice: Subject to any disclaimer, the term of this patent is extended or adjusted under 35 U.S.C. 154(b) by 799 days.

(21) Appl. No.: 17/778,958

(22) PCT Filed: Nov. 25, 2020

(86) PCT No.: PCT/US2020/062325
§ 371 (c)(1),
(2) Date: May 23, 2022

(87) PCT Pub. No.: WO2021/108632
PCT Pub. Date: Jun. 3, 2021

(65) Prior Publication Data
US 2023/0026693 A1    Jan. 26, 2023

Related U.S. Application Data

(60) Provisional application No. 62/939,724, filed on Nov. 25, 2019.

(51) Int. Cl.
*C12P 19/34* (2006.01)
*C12N 9/12* (2006.01)

(52) U.S. Cl.
CPC ............ *C12P 19/34* (2013.01); *C12N 9/1252* (2013.01); *C12Y 207/07007* (2013.01)

(58) Field of Classification Search
CPC ....................... C12N 9/1252; C12Y 207/07007
See application file for complete search history.

(56) References Cited

U.S. PATENT DOCUMENTS

| | | | |
|---|---|---|---|
| 4,935,449 A | 6/1990 | Bey et al. | |
| 5,614,365 A | 3/1997 | Tabor et al. | |
| 5,889,061 A | 3/1999 | Frydman et al. | |
| 2013/0253034 A1 | 9/2013 | Gryaznov et al. | |
| 2014/0186894 A1 | 7/2014 | Liu et al. | |
| 2024/0309418 A1 | 9/2024 | Lelyveld et al. | |

FOREIGN PATENT DOCUMENTS

| | | |
|---|---|---|
| WO | WO 1998/017624 | 4/1998 |
| WO | WO 2000/066175 | 11/2000 |
| WO | WO 2000/066587 | 11/2000 |
| WO | WO 2002/010142 | 2/2002 |
| WO | WO 2021/108632 | 6/2021 |

OTHER PUBLICATIONS

Arangundy-Franklin et al., "A synthetic genetic polymer with an uncharged backbone chemistry based on alkyl phosphonate nucleic acids," Europe PMC Public Access Author Manuscript, doi: 10.1038/s41557-019-0255-4, published online Oct. 22, 2019; published in final edited form as: Nature Chemistry, Jun. 2019, 11(6):533-542, 26 pages.

Castro et al., "Nucleic acid polymerases use a general acid for nucleotidyl transfer," Nat Struct Mal Biol., Feb. 2009, 16(2):212-218.

Chim et al., "Crystal structures of DNA polymerase I capture novel intermediates in the DNA synthesis pathway," eLife, Oct. 2018, 7:e40444, 11 pages.

Eckstein, "Nucleoside Phosphorothioates," Annual Review of Biochemistry, 1985, 54:367-402.

Freund et al., "New chemistries and enzymes for synthetic genetics," Current Opinion in Biotechnology, Apr. 2022, 74:129-136.

Gryaznov, "Oligonucleotide N3 '→>PS' phosphoramidates as antisense agents," Nucleic Acids Research, Apr. 1996, 24(8):1508-1514.

Hanna et al., "A phosphoramidate substrate analog is a competitive inhibitor of the Tetrahymena group I ribozyme," Chemistry & Biology, Nov. 2000, 7(11):845-854.

Henry et al., "The evolution of DNA polymerases with novel activities," Current Opinion in Biotechnology, Aug. 2005, 16(4):370-377.

Herschlag et al., "Ribozyme-catalyzed and nonenzymic reactions of phosphate diesters: rate effects upon substitution of sulfur for a nonbridging phosphoryl oxygen atom," Biochemistry, May 1991, 30(20):4844-4854.

International Search Report and Written Opinion in International Appln. No. PCT/US2024/019980, mailed on Aug. 15, 2024, 13 pages.

Johnson, "The kinetic and chemical mechanism of high-fidelity DNA polymerases," HHS Public Access Author Manuscript, doi: 10.1016/j.bbapap.2010.01.006, published online May 1, 2011; published in final edited form as: Biochimica et Biophysica Acta (BEA)—Proteins and Proteomics, May 2010, 1804(5):1041-1048, 21 pages.

Joyce et al., "DNA Polymerase Fidelity: Kinetics, Structure, and Checkpoints," Biochemistry, Nov. 2004, 43(45):14317-14324, 7 pages.

Letsinger et al., "Nucleotide chemistry. XVII. Enzymic synthesis of polydeoxyribonucleotides possessing internucleotide phosphoramidate bonds," Journal of the American Chemical Society, Jan. 1972, 94(1):292-293.

Li et al., "Nucleoside and Oligonucleoside Boranophosphates: Chemistry and Properties," Chem. Rev., Oct. 2007, 107(11):4746-4796.

Lohrmann et al., "Template-directed synthesis of high molecular weight polynucleotide analogues," Nature, May 1976, 261:342-344.

(Continued)

*Primary Examiner* — Robert J Yamasaki
(74) *Attorney, Agent, or Firm* — Fish & Richardson P.C.

(57) ABSTRACT

Provided herein, in some embodiments, are enzymatic methods for producing an oligonucleotide comprising phosphoramidate-linked nucleotides, and compositions comprising the oligonucleotide thus produced.

24 Claims, 26 Drawing Sheets
Specification includes a Sequence Listing.

(56) References Cited

OTHER PUBLICATIONS

Marton et al., "Polyamines as targets for therapeutic intervention," Ann. Rev. Pharm. Toxicol., 1995, 35:55-91.
Mukhopadhyay et al., "Effects of Bis(benzyl)polyamine analogs on Leishmania donovani promastigotes," Exp. Parasit., Aug. 1995, 81(1):39-46.
Nakamura et al., "Watching DNA polymerase η make a phosphodiester bond," HHS Public Access Author Manuscript, doi: 10.1038/nature11181, published online Jan. 12, 2013; published in final edited form as: Nature, Jul. 2012, 487(7406):196-201, 15 pages.
Oertell et al., "Transition state in DNA polymerase β catalysis: rate-limiting chemistry altered by base-pair configuration," Biochemistry, Mar. 2014, 53(11):1842-1848.
Osland et al., "Influence of polyamines on the activity of DNA polymerase I from *Escherichia coli*," Biochimica et Biophysica Acta (BEA)—Nucleic Acids and Protein Synthesis, Sep. 1978, 520(2):317-330.
O'Sullivan et al., "Polyamine derivatives as inhibitors of trypanothione reductase and assessment of their trypanocidal activities," Bioorg. Med Chem., Dec. 1997, 5(12):2145-2155.
Samara et al., "Detection of Reaction Intermediates in $Mg^{2+}$-Dependent DNA Synthesis and RNA Degradation by Time-Resolved X-Ray Crystallography," HHS Public Access Author Manuscript, doi: 10.1016/bs.mie.2017.03.022, published online Aug. 17, 2018; published in final edited form as: Methods in Enzymology, 2017, 592:283-327, 43 pages.
Steitz, "A mechanism for all polymerases," Nature, Jan. 1998, 391(6664):231-232.
Sucato et al., "DNA Polymerase β Fidelity: Halomethylene-Modified Leaving Groups in Pre-Steady-State Kinetic Analysis Reveal Differences at the Chemical Transition State," Biochemistry, Dec. 2007, 47(3):870-879.
Taylor et al., "Directed evolution of artificial enzymes (XNAzymes) from diverse repertoires of synthetic genetic polymers," Nat Protoc., Oct. 2015, 10(10):1625-1642.
Vashishtha et al., "Different Divalent Cations Alter the Kinetics and Fidelity of DNA Polymerases," Journal of Biological Chemistry, Sep. 2016, 291(40):20869-20875.
Wood, "The aqueous geochemistry of the rare-earth elements: Critical stability constants for complexes with simple carboxylic acids at 25° C. and 1 bar and their application to nuclear waste management," Engineering Geology, Sep. 1993, 34(3-4):229-259.
Wu et al., "How DNA polymerases catalyse replication and repair with contrasting fidelity," Nat Rev Chem., Sep. 2017, 1:0068, 16 pages.
Zielinski et al., "Oligomerization of activated derivatives of 3'-amino-3'-deoxyguanosine on poly(C) and poly(dC) templates," Nucleic Acids Research, Apr. 1985, 13(7):2469-2484.
Björkbom et al., "Bidirectional Direct Sequencing of Noncanonical RNA by Two-Dimensional Analysis of Mass Chromatograms," J. Am. Chem. Soc., 2015, 137:14430-14438.
Blain et al., "Synthesis and Nonenzymatic Template-Directed Polymerization of 2'-Amino-2'-deoxythreose Nucleotides," J. Am. Chem. Soc., Feb. 2014, 136(5):2033-2039.
Cagri Izgu et al., "Synthesis of activated 3'-amino-3'-deoxy-2-thiothymidine, a superior substrate for the nonenzymatic copying of nucleic acid templates," Chem. Commun., 2016, 52:3684-3686.
Castro et al., "Two proton transfers in the transition state for nucleotidyl transfer catalyzed by RNA- and DNA-dependent RNA and DNA polymerases," Proc. Natl. Acad Sci., 2007, 104(11):4267-4272.
Chaput and Szostak, "TNA Synthesis by DNA Polymerases," J. Am. Chem. Soc., 2003, 125(31):9274-9275.
Chen et al., "N2'→P3' Phosphoramidate Glycerol Nucleic Acid as a Potential Alternative Genetic System," J. Am. Chem. Soc., 2009, 131(6):2119-2121.
Cheng et al., "Human immunodeficiency virus reverse transcriptase. General properties and its interactions with nucleoside triphosphate analogs," J. Biol. Chem., 1987, 262(5):2187-2189.
Chidgeavadze et al., "2',3'-Dideoxy-3' aminonucleoside 5'-triphosphates are the terminators of DNA synthesis catalyzed by DNA polymerases," Nucleic Acids Res., 1984, 12:1671-1686.
Ding et al., "An Oligodeoxyribonucleotide N3'→P5' Phosphoramidate Duplex Forms an A-type Helix in Solution," Nucleic Acids Res., 1996, 24(2):354-360.
Eschenmoser, "Chemical Etiology of Nucleic Acid Structure," Science, 1999, 284(5423):2118-24.
Fleischmann et al., "Whole-genome comparison of *Mycobacterium tuberculosis* clinical and laboratory strains," Journal of Bacteriology, Oct. 2002, 184(19):5479-5490.
Golosov et al., "The Mechanism of the Translocation Step in DNA Replication by DNA Polymerase I: A Computer Simulation Analysis," Structure, Jan. 2010, 18(1):83-93.
Handlon and Oppenheimer, "Thiol Reduction of 3'-Azidothymidine to 3'-Aminothymidine: Kinetics and Biomedical Implications," Pharm. Res., May 1988, 5(5):297-299.
Inouye, "On the Prediction of $pK_a$ Values of Amino Sugars," Chem. Pharm. Bull. (Tokyo), 1968, 16(6):1134-1137.
International Preliminary Report on Patentability in International Appln. No. PCT/US2020/062325, mailed on Jun. 9, 2022, 7 pages.
International Search Report and Written Opinion in International Appln. No. PCT/US2020/062325, mailed on Mar. 31, 2021, 10 pages.
Irimia et al., "Calcium Is a Cofactor of Polymerization but Inhibits Pyrophosphorolysis by the Sulfolobus solfataricus DNA Polymerase Dpo4," Biochemistly, May 2006, 45(19):5949-5956.
Johnson et al., "Processive DNA synthesis observed in a polymerase crystal suggests a mechanism for the prevention of frameshift mutations," Proc. Natl. Acad. Sci., Mar. 2003, 100(7):3895-3900.
Joyce, "Choosing the right sugar: How polymerases select a nucleotide substrate," Proc. Natl. Acad. Sci., Mar. 1997, 94(5):1619-1622.
Kervio et al., "Templating efficiency of naked DNA," Proc. Natl. Acad Sci., Jul. 2010, 107(27):12074-12079.
Kiefer et al., "Crystal structure of a thermostable Bacillus DNA polymerase I large fragment at 2.1 [angstrom] resolution," Structure, Jan. 1997, 5(1):95-108.
Kiefer et al., "Visualizing DNA replication in a catalytically active Bacillus DNA polymerase crystal," Nature, Jan. 1998, 391(6664):304-307.
Kim et al., "A model for the emergence of RNA from a prebiotically plausible mixture of ribonucleotides, arabinonucleotides and 2'-deoxynucleotides," J Am. Chem. Soc., Jan. 2020, 142(5):2317-2326.
Lelyveld et al., "DNA polymerase activity on synthetic N3'→P5' phosphoramidate DNA templates," Nucleic Acids Res., Sep. 2019, 47(17):8941-8949, 9 pages.
Lelyveld et al., "Synthesis of phosphoramidate-linked DNA by a modified DNA polymerase," Proceedings of the National Academy of Sciences of the U.S.A., Mar. 2020, 117(13):7276-7283.
Mansy et al., "Template-directed synthesis of a genetic polymer in a model protocell," Nature, Jun. 2008, 454:122-125.
O'Flaherty et al., "Nonenzymatic Template-Directed Synthesis of Mixed-Sequence 3-NP-DNA up to 25 Nucleotides Long Inside Model Protocells," Journal of the American Chemical Society, Jun. 2019, 141(26):10481-10488.
Ralec et al., "Calcium-driven DNA synthesis by a high-fidelity DNA polymerase," Nucleic Acids Res., Oct. 2017, 45(21):12425-12440.
Shuman, "DNA Ligases: Progress and Prospects," J. Biol. Chem., Jun. 2009, 284(26):17365-17369.
Steitz et al., "A unified polymerase mechanism for nonhomologous DNA and RNA polymerases," Sci. Wash., Dec. 1994, 266(5193):2022-5.
Tabor and Richardson, "A single residue in DNA polymerases of the *Escherichia coli* DNA polymerase I family is critical for distinguishing between deoxy- and dideoxyribonucleotides," Proc. Natl. Acad. Sci., Jul. 1995, 92(14):6339-6343.
Tereshko et al., "Consequences of Replacing the DNA 3'-Oxygen by an Amino Group: High-Resolution Crystal Structure of a Fully Modified N3'→P5' hosphoramidate DNA Dodecamer Duplex," J Am. Chem. Soc., 1998, 120(2):269-283.

(56) References Cited

OTHER PUBLICATIONS

Uniprot Accession No. D9N168, "Full=DNA polymerase I," Oct. 10, 2018, 2 pages.
Uniprot Accession No. P00581, "Full=DNA-directed DNA polymerase," Oct. 10, 2018, 6 pages.
Uniprot Accession No. P00582, "Full=DNA polymerase I," Mar. 28, 2018, 6 pages.
Uniprot Accession No. P19821, "Full=DNA polymerase I, thermostable," Oct. 10, 2018, 6 pages.
Uniprot Accession No. P19822, "Full=DNA polymerase," May 23, 2018, 3 pages.
Uniprot Accession No. P52026.2, "Full=DNA polymerase I; Short=POL I," Feb. 10, 2021, 9 pages.
Uniprot Accession No. P52028, "Full=DNA polymerase I, thermostable," Mar. 28, 2018, 2 pages.
Uniprot Accession No. P54098, "Full=DNA polymerase subunit gamma-1," Sep. 12, 2018, 16 pages.
Wang et al., "Structural factors that determine selectivity of a high fidelity DNA polymerase for deoxy-, dideoxy-, and ribonucleotides," J. Biol. Chem., Aug. 2012, 287(34):28215-28226.
Warren et al., "The structural basis for the mutagenicity of $O^6$-methylguanine lesions," Proc. Natl. Acad. Sci., Dec. 2006, 103(52):19701-19706.
Wu et al., "The Structure of a High Fidelity DNA Polymerase Bound to a Mismatched Nucleotide Reveals an "Ajar" Intermediate Conformation in the Nucleotide Selection Mechanism," The Journal of Biological Chemistry, Jun. 2011, 286(22):19758-19767.
Zhang et al., "Fast and accurate nonenzymatic copying of an RNA-like synthetic genetic polymer," Proc. Natl. Acad Sci., Oct. 2013, 110(44):17732-17737.
Zhang et al., "Synthesis of N3'-P5'-linked Phosphoramidate DNA by Nonenzymatic Template-Directed Primer Extension," J. Am. Chem. Soc., Jan. 2013, 135(2):924-932.
Zhang et al., "Template-Directed Nonenzymatic Primer Extension Using 2-Methylimidazole-Activated Morpholino Derivatives of Guanosine and Cytidine," J. Am. Chem. Soc., Jul. 2019, 141(30):12159-12166.

SEQUENCE LISTING

<160> NUMBER OF SEQ ID NOS: 7

<210> SEQ ID NO 1
<211> LENGTH: 876
<212> TYPE: PRT
<213> ORGANISM: Bacillus stearothermophilus

<400> SEQUENCE: 1

```
Met Lys Asn Lys Leu Val Leu Ile Asp Gly Asn Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Gln Pro Thr His Ile Leu Val Ala Phe Asp Ala Gly Lys Thr Thr
    50                  55                  60

Phe Arg His Glu Thr Phe Gln Asp Tyr Lys Gly Gly Arg Gln Gln Thr
65                  70                  75                  80

Pro Pro Glu Leu Ser Glu Gln Phe Pro Leu Leu Arg Glu Leu Leu Lys
                85                  90                  95

Ala Tyr Arg Ile Pro Ala Tyr Glu Leu Asp His Tyr Glu Ala Asp Asp
            100                 105                 110

Ile Ile Gly Thr Met Ala Ala Arg Ala Glu Arg Glu Gly Phe Ala Val
        115                 120                 125

Lys Val Ile Ser Gly Asp Arg Asp Leu Thr Gln Leu Ala Ser Pro Gln
    130                 135                 140

Val Thr Val Glu Ile Thr Lys Lys Gly Ile Thr Asp Ile Glu Ser Tyr
145                 150                 155                 160

Thr Pro Glu Thr Val Val Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Lys Gln Phe
        195                 200                 205

Gly Thr Val Glu Asn Val Leu Ala Ser Ile Asp Glu Ile Lys Gly Glu
    210                 215                 220

Lys Leu Lys Glu Asn Leu Arg Gln Tyr Arg Asp Leu Ala Leu Leu Ser
225                 230                 235                 240

Lys Gln Leu Ala Ala Ile Cys Arg Asp Ala Pro Val Glu Leu Thr Leu
                245                 250                 255

Asp Asp Ile Val Tyr Lys Gly Glu Asp Arg Glu Lys Val Val Ala Leu
            260                 265                 270

Phe Gln Glu Leu Gly Phe Gln Ser Phe Leu Asp Lys Met Ala Val Gln
        275                 280                 285

Thr Asp Glu Gly Glu Lys Pro Leu Ala Gly Met Asp Phe Ala Ile Ala
    290                 295                 300

Asp Ser Val Thr Asp Glu Met Leu Ala Asp Lys Ala Ala Leu Val Val
305                 310                 315                 320

Glu Val Val Gly Asp Asn Tyr His His Ala Pro Ile Val Gly Ile Ala
                325                 330                 335

Leu Ala Asn Glu Arg Gly Arg Phe Phe Leu Arg Pro Glu Thr Ala Leu
            340                 345                 350

Ala Asp Pro Lys Phe Leu Ala Trp Leu Gly Asp Glu Thr Lys Lys Lys
        355                 360                 365
```

```
Thr Met Phe Asp Ser Lys Arg Ala Ala Val Ala Leu Lys Trp Lys Gly
    370                 375                 380
Ile Glu Leu Arg Gly Val Val Phe Asp Leu Leu Leu Ala Ala Tyr Leu
385                 390                 395                 400
Leu Asp Pro Ala Gln Ala Ala Gly Asp Val Ala Val Ala Lys Met
                    405                 410                 415
His Gln Tyr Glu Ala Val Arg Ser Asp Glu Ala Val Tyr Gly Lys Gly
                420                 425                 430
Ala Lys Arg Thr Val Pro Asp Glu Pro Thr Leu Ala Glu His Leu Val
                435                 440                 445
Arg Lys Ala Ala Ala Ile Trp Ala Leu Glu Glu Pro Leu Met Asp Glu
    450                 455                 460
Leu Arg Arg Asn Glu Gln Asp Arg Leu Leu Thr Glu Leu Glu Gln Pro
465                 470                 475                 480
Leu Ala Gly Ile Leu Ala Asn Met Glu Phe Thr Gly Val Lys Val Asp
                    485                 490                 495
Thr Lys Arg Leu Glu Gln Met Gly Ala Glu Leu Thr Glu Gln Leu Gln
                500                 505                 510
Ala Val Glu Arg Arg Ile Tyr Glu Leu Ala Gly Gln Glu Phe Asn Ile
    515                 520                 525
Asn Ser Pro Lys Gln Leu Gly Thr Val Leu Phe Asp Lys Leu Gln Leu
530                 535                 540
Pro Val Leu Lys Lys Thr Lys Thr Gly Tyr Ser Thr Ser Ala Asp Val
545                 550                 555                 560
Leu Glu Lys Leu Ala Pro His His Glu Ile Val Glu His Ile Leu His
                565                 570                 575
Tyr Arg Gln Leu Gly Lys Leu Gln Ser Thr Tyr Ile Glu Gly Leu Leu
                580                 585                 590
Lys Val Val His Pro Val Thr Gly Lys Val His Thr Met Phe Asn Gln
    595                 600                 605
Ala Leu Thr Gln Thr Gly Arg Leu Ser Ser Val Glu Pro Asn Leu Gln
    610                 615                 620
Asn Ile Pro Ile Arg Leu Glu Glu Gly Arg Lys Ile Arg Gln Ala Phe
625                 630                 635                 640
Val Pro Ser Glu Pro Asp Trp Leu Ile Phe Ala Ala Asp Tyr Ser Gln
                645                 650                 655
Ile Glu Leu Arg Val Leu Ala His Ile Ala Glu Asp Asp Asn Leu Ile
                660                 665                 670
Glu Ala Phe Arg Arg Gly Leu Asp Ile His Thr Lys Thr Ala Met Asp
    675                 680                 685
Ile Phe His Val Ser Glu Glu Asp Val Thr Ala Asn Met Arg Arg Gln
    690                 695                 700
Ala Lys Ala Val Asn Phe Gly Ile Val Tyr Gly Ile Ser Asp Tyr Gly
705                 710                 715                 720
Leu Ala Gln Asn Leu Asn Ile Thr Arg Lys Glu Ala Ala Glu Phe Ile
                725                 730                 735
Glu Arg Tyr Phe Ala Ser Phe Pro Gly Val Lys Gln Tyr Met Asp Asn
                740                 745                 750
Ile Val Gln Glu Ala Lys Gln Lys Gly Tyr Val Thr Thr Leu Leu His
    755                 760                 765
Arg Arg Arg Tyr Leu Pro Asp Ile Thr Ser Arg Asn Phe Asn Val Arg
    770                 775                 780
Ser Phe Ala Glu Arg Thr Ala Met Asn Thr Pro Ile Gln Gly Ser Ala
```

```
                             785                 790                 795                 800
Ala Asp Ile Ile Lys Lys Ala Met Ile Asp Leu Ser Val Arg Leu Arg
                    805                 810                 815

Glu Glu Arg Leu Gln Ala Arg Leu Leu Leu Gln Val His Asp Glu Leu
                820                 825                 830

Ile Leu Glu Ala Pro Lys Glu Ile Glu Arg Leu Cys Arg Leu Val
            835                 840                 845

Pro Glu Val Met Glu Gln Ala Val Thr Leu Arg Val Pro Leu Lys Val
        850                 855                 860

Asp Tyr His Tyr Gly Pro Thr Trp Tyr Asp Ala Lys
865                 870                 875

<210> SEQ ID NO 2
<211> LENGTH: 9
<212> TYPE: DNA
<213> ORGANISM: Artificial Sequence
<220> FEATURE:
<223> OTHER INFORMATION: synthetic primer
<220> FEATURE:
<221> NAME/KEY: modified_base
<222> LOCATION: (9)..(9)
<223> OTHER INFORMATION: 3'-amino-2',3'-dideoxycytidine (nC) or
      2',3'-Dideoxycytidine (ddC)

<400> SEQUENCE: 2 gcgatcagc                                                                 9

<210> SEQ ID NO 3
<211> LENGTH: 14
<212> TYPE: DNA
<213> ORGANISM: Artificial Sequence
<220> FEATURE:
<223> OTHER INFORMATION: synthetic primer

<400> SEQUENCE: 3
acacgctgat cgca                                                          14

<210> SEQ ID NO 4
<211> LENGTH: 18
<212> TYPE: DNA
<213> ORGANISM: Artificial Sequence
<220> FEATURE:
<223> OTHER INFORMATION: 3'-amino terminal DNA primer

<400> SEQUENCE: 4
gcgtccattc gttacctg                                                      18

<210> SEQ ID NO 5
<211> LENGTH: 23
<212> TYPE: DNA
<213> ORGANISM: Artificial Sequence
<220> FEATURE:
<223> OTHER INFORMATION: synthetic template

<400> SEQUENCE: 5
cgcaggtaag caatggacgg act                                                23

<210> SEQ ID NO 6
<211> LENGTH: 46
<212> TYPE: DNA
<213> ORGANISM: Artificial Sequence
<220> FEATURE:
<223> OTHER INFORMATION: synethetic template

<400> SEQUENCE: 6
```

```
cgcaggtaag caatggacgg actacgcact cataagttgt aaaggc              46
```

<210> SEQ ID NO 7
<211> LENGTH: 24
<212> TYPE: DNA
<213> ORGANISM: Artificial Sequence
<220> FEATURE:
<223> OTHER INFORMATION: synthetic template

<400> SEQUENCE: 7

```
cgcgaattcg cgcgcgaatt cgcg                                      24
```

US 12,428,658 B2

METHODS AND COMPOSITIONS FOR ENZYMATIC POLYMERIZATION OF N3'→P5' PHOSPHORAMIDATE DNA

CLAIM OF PRIORITY

This application is a U.S. National Phase Application under 35 U.S.C. § 371 of International Patent Application No. PCT/US2020/062325, filed on Nov. 25, 2020, which claims the benefit of U.S. Provisional Patent Application No. 62/939,724, filed on Nov. 25, 2019, which is incorporated by reference herein in its entirety.

SEQUENCE LISTING

This application contains a Sequence Listing that has been submitted electronically as an ASCII text file named 'Sequence_Listing'. The ASCII text file, created on May 19, 2022, is 8.94 kilobytes in size. The material in the ASCII text file is hereby incorporated by reference in its entirety.

FIELD OF THE INVENTION

The subject matter disclosed herein generally relates to oligonucleotides comprising N3'→P5' phosphoramidate (NP) bonds, and enzymatic methods for producing such.

BACKGROUND OF THE INVENTION

DNA polymerases copy genetic material by catalyzing phosphodiester bond formation. This highly conserved activity proceeds by a common mechanism, such that incorporated nucleoside analogs terminate chain elongation if the resulting primer strand lacks a terminal hydroxyl group. Even conservatively substituted 3'-amino nucleotides generally act as chain terminators, and no enzymatic pathway for their polymerization has yet been found. Although 3'-amino nucleotides can be chemically coupled to yield stable oligonucleotides containing N3'→P5' phosphoramidate (NP) bonds, no such internucleotide linkages are known to be enzymatically synthesized and to occur in nature.

SUMMARY OF THE INVENTION

The present disclosure is based, at least in part, on the surprising discovery that 3'-amino terminated primers can be extended by DNA polymerase from *B. stearothermophilus* in a template-directed manner to produce oligonucleotides comprising N3'→P5' phosphoramidate (NP) bonds. It has also been demonstrated that faster rates of extension can be achieved with $Ca^{2+}$ rather than $Mg^{2+}$ or other metal ion cofactors and/or with DNA polymerase comprising a single active site mutation.

Accordingly, aspects of the present disclosure provide a method for producing an oligonucleotide comprising phosphoramidate-linked nucleotides, the method comprising incubating a sample comprising a DNA polymerase variant comprising an amino acid sequence that is at least 70% identical to SEQ ID NO: 1, wherein the amino acid sequence comprises an amino acid substitution at position F710, a divalent metal ion cofactor, 3'-amino-2',3'-dideoxyribonucleotide 5'-triphosphates (nNTPs), a 3'-amino terminated primer, and a DNA template comprising, from 3' to 5', a sequence complementary to the primer and a nucleic acid sequence of interest, under conditions and for a time sufficient for the DNA polymerase variant to produce the oligonucleotide comprising phosphoramidate-linked nucleotides.

In some embodiments, the amino acid sequence is at least 80% identical to SEQ ID NO: 1. In some embodiments, the amino acid sequence is at least 90% identical to SEQ ID NO: 1. In some embodiments, the amino acid sequence is at least 95% identical to SEQ ID NO: 1. In some embodiments, the amino acid substitution at position F710 is F710Y. In some embodiments, the DNA polymerase variant comprises the amino acid sequence set forth in SEQ ID NO: 1.

In some embodiment, the DNA polymerase variant is prepared from cells that express the DNA polymerase variant. In some embodiments, the DNA polymerase variant is in a cell lysate from cells that express the DNA polymerase variant.

In some embodiments, the sample is incubated at a temperature of 50 to 65° C. In some embodiments, the sample is incubated at a temperature of 55° C.

In some embodiments, the sample is incubated for 1 to 24 hours. In some embodiments, the sample is incubated for 24 hours.

In some embodiments, the sample is incubated at a pH of 7 to 10. In some embodiments, the sample is incubated at a pH of 8.6-9.2. In some embodiments, the sample is incubated at a pH of 8.8.

In some embodiments, the divalent metal ion cofactor is selected from the group consisting of $Ba^{2+}$, $Sr^{2+}$, $Ca^{2+}$, $Mg^{2+}$, $Mn^{2+}$, $Co^{2+}$, and $Zn^{2+}$. In some embodiments, the divalent metal ion cofactor is $Ca^{2+}$.

In some embodiments, the nNTPs comprise nATP, nGTP, nCTP, and/or nTTP.

In some embodiments, the 3'-amino terminated primer comprises ribonucleotides and/or deoxyribonucleotides.

In some embodiments, the 3'-amino terminated primer comprises a 3'-amino terminal ribonucleotide selected from the group consisting of 3'-amino-adenosine, 3'-amino-guanosine, 3'-amino-cytidine, and 3'-amino-uridine.

In some embodiments, the 3'-amino terminated primer comprises a 3'-amino terminal dideoxynucleotide selected from the group consisting of 3'-amino-2',3'-dideoxyadenosine (nA), 3'-amino-2',3'-dideoxythymidine (nT), 3'-amino-2',3'-dideoxycytidine (nC), or 3'-amino-2',3'-dideoxyguanosine (nG).

In some embodiments, the 3'-amino terminated primer comprises a label.

In some embodiments, the 3'-amino terminated primer comprises phosphodiester-linked nucleotides and/or phosphoramidate-linked nucleotides.

In some embodiments, the 3'-amino terminated primer is 5 to 200 nucleotides in length.

In some embodiments, the 3'-amino terminated primer comprises at least 5 consecutive phosphoramidate-linked nucleotides. In some embodiments, the 3'-amino terminated primer comprises at least 25 consecutive phosphoramidate-linked nucleotides.

In some embodiments, each nucleotide in the 3'-amino terminated primer is phosphoramidate-linked.

In some embodiments, the oligonucleotide is 25 to 250 nucleotides in length.

In some embodiments, the oligonucleotide comprises phosphoramidate-linked nucleotides and phosphodiester-linked nucleotides.

In some embodiments, the oligonucleotide comprises at least 25 consecutive phosphoramidate-linked nucleotides. In some embodiments, the oligonucleotide comprises at least 50 consecutive phosphoramidate-linked nucleotides. In some embodiments, the oligonucleotide comprises at least 100 consecutive phosphoramidate-linked nucleotides. In some embodiments, each nucleotide in the oligonucleotide is phosphoramidate-linked.

In some embodiments, the sample further comprises nucleoside triphosphates (NTPs). In some embodiments, the NTPs comprise deoxynucleoside triphosphates (dNTPs).

Aspects of the present disclosure provide an oligonucleotide comprising a plurality of phosphoramidate linkages, wherein the oligonucleotide is 25 to 250 nucleotides in length.

In some embodiments, the oligonucleotide is 25 to 150 nucleotides in length. In some embodiments, the oligonucleotide is 25 to 100 nucleotides in length.

In some embodiments, the oligonucleotide comprises phosphoramidate-linked nucleotides and phosphodiester-linked nucleotides.

In some embodiments, the oligonucleotide comprises at least 25 consecutive phosphoramidate-linked nucleotides. In some embodiments, the oligonucleotide comprises at least 50 consecutive phosphoramidate-linked nucleotides. In some embodiments, the oligonucleotide comprises at least 100 consecutive phosphoramidate-linked nucleotides. In some embodiments, each nucleotide in the oligonucleotide is phosphoramidate-linked.

In some embodiments, the oligonucleotide comprises ribonucleotides and/or deoxyribonucleotides.

The details of one or more embodiments of the invention are set forth in the description below. Other features or advantages of the present invention will be apparent from the following drawings and detailed description of several embodiments, and also from the appended claims.

DETAILED DESCRIPTION

The present disclosure provides, in some aspects, methods for enzymatic synthesis of oligonucleotides comprising phosphoramidate-linked nucleotides, and compositions comprising such. The enzymatic methods described herein led to at least the following advantageous outcomes compared to known synthetic methods including increased yield, increased efficiency, the use of stable aqueous substrates, and greater numbers of consecutive phosphoramidate-linked nucleotides in the oligonucleotide thus produced.

Provided herein are methods involving a DNA polymerase variant (e.g., a DNA polymerase variant comprising a F710Y mutation) that extends 3'-amino terminal primers in a template-directed manner to produce oligonucleotides comprising N3'→N5' phosphoramidate (NP) bonds. Methods described herein can comprise $Ca^{2+}$ as a cofactor, which increased NP activity of the DNA polymerase variant by 5-fold compared to NP activity in the presence of $Mg^{2+}$. When $Ca^{2+}$ was used as the cofactor, the NP activity of the DNA polymerase variant was 21-fold faster than that of the wild-type DNA polymerase. Accordingly, methods described herein utilize a DNA polymerase variant and a divalent metal ion cofactor to produce oligonucleotides comprising phosphoramidate-linked nucleotides.

Figure 4A:
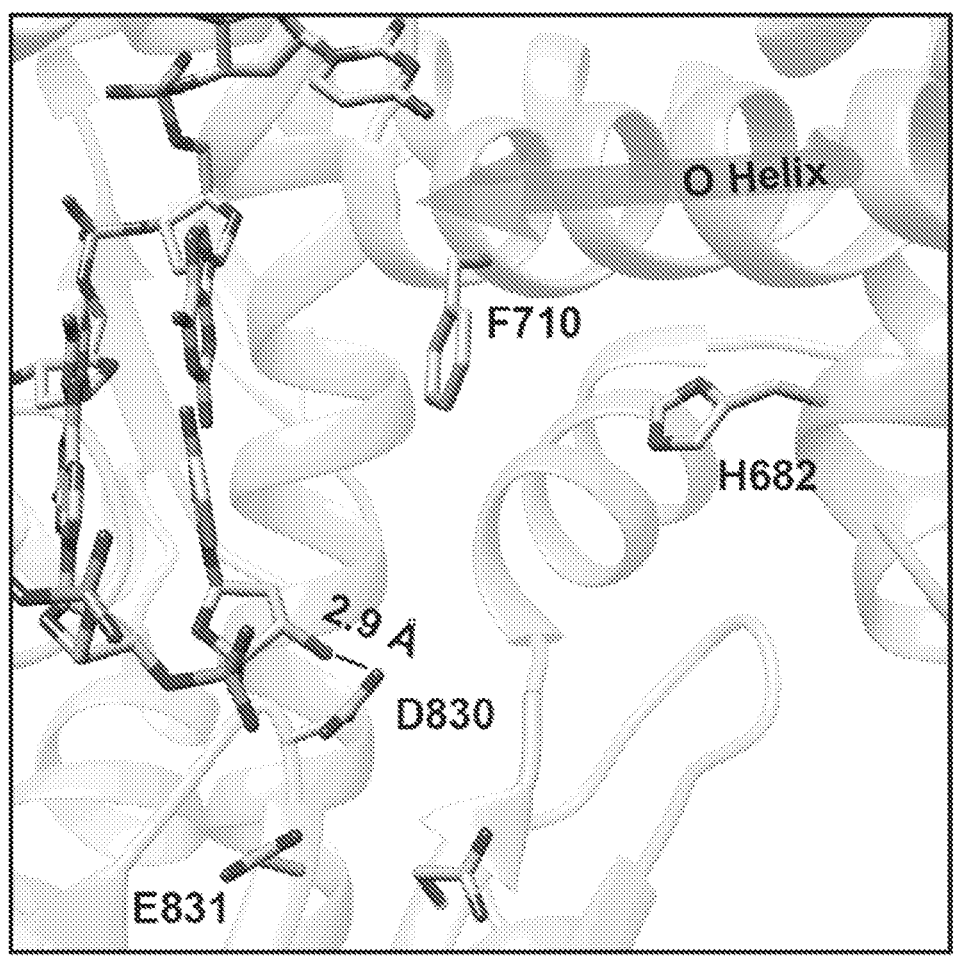
FIG. 4A show the reactant "0 complex" in the open conformation, with bound DNA duplex containing a 3'-amino terminal primer aligned at the active site, as in FIGS. 1B-1C (PDB 6UR4).
Figure 4B:
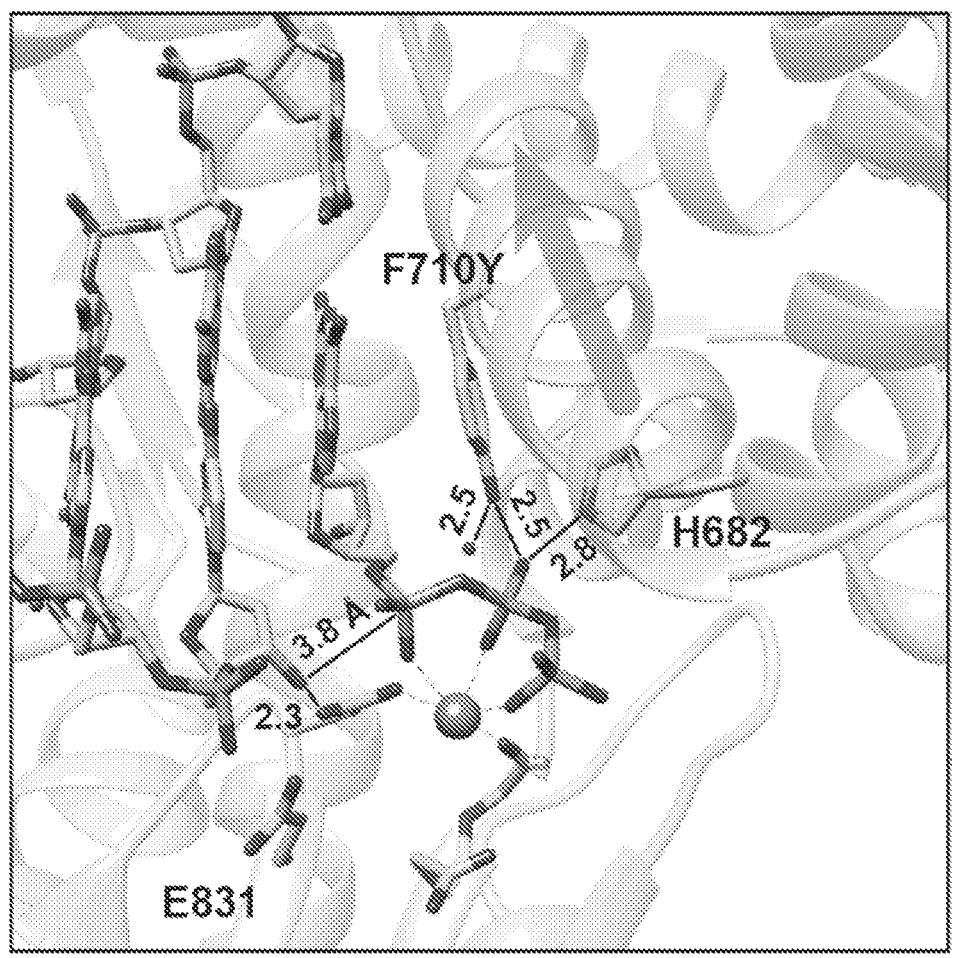
FIG. 4B shows the closed conformation reaction complex bound to DNA duplex containing a 3'-amino terminal primer, substrate analog dGpNHpp, and $Mn^{2+}$ (PDB 6US5).
Figure 4C:
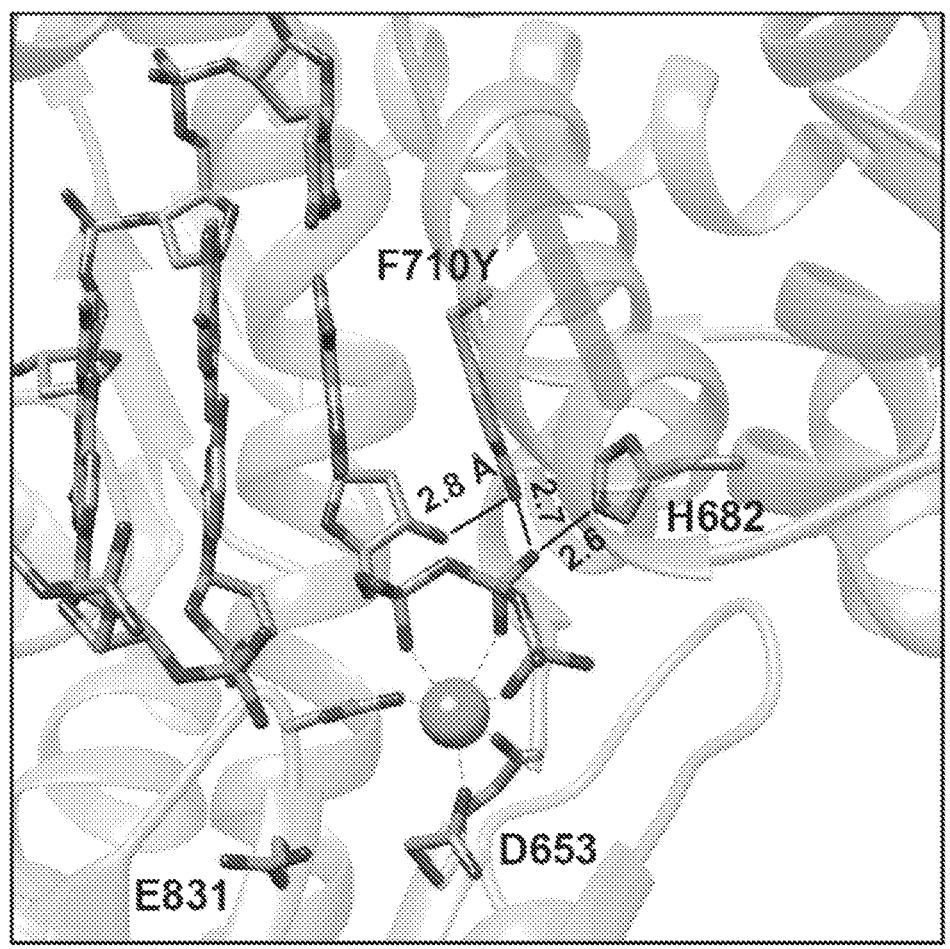
FIG. 4C shows the closed conformation reaction complex bound to DNA duplex containing a 3'-dideoxy terminal primer, as well as nGTP substrate and $Ca^{2+}$ (6UR9).

Studies described herein demonstrate that BF can use both deoxyribonucleoside triphosphate (dNTP) and 3'-amino-2', 3'-dideoxyribonucleoside triphosphate (nNTP) substrates in 3'-amino extension reactions. In some illustrative instances, BF was selective for dCTP over nCTP in 3'-amino extension reactions. This selectivity is modulated by mutations in the polymerase active site, notably the mutation F710Y in the "O-helix" of the fingers domain (Table 4). Without wishing to be bound by theory, this selectivity might be due, in part, from structural differences between the bound substrate geometry of nGTP seen in the crystal structure compared to that observed for the unreactive dGTP analog (FIGS. 4B-4C). Without wishing to be bound by theory, tuning of the reactivity of the substrate appears to be conferred not only by triphosphate-metal coordination, but also by side chains in the fingers domain that interact directly with the bound substrate in the closed conformation.

Figure 3A:
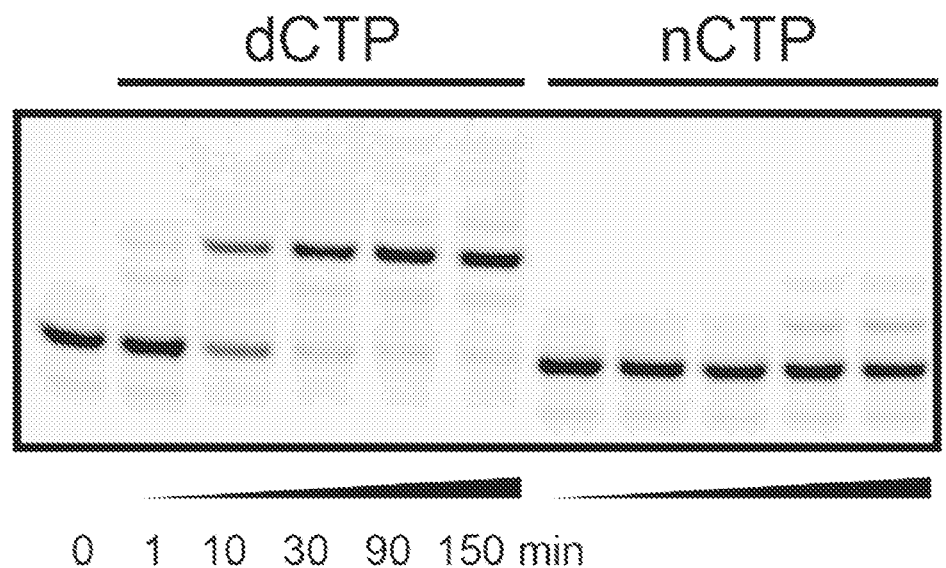
FIG. 3A shows a time course of 3'-amino primer extension with either 1 mM dCTP or nCTP with wild-type BF and conditions as in FIGS. 2A-2D.
Figure 3B:
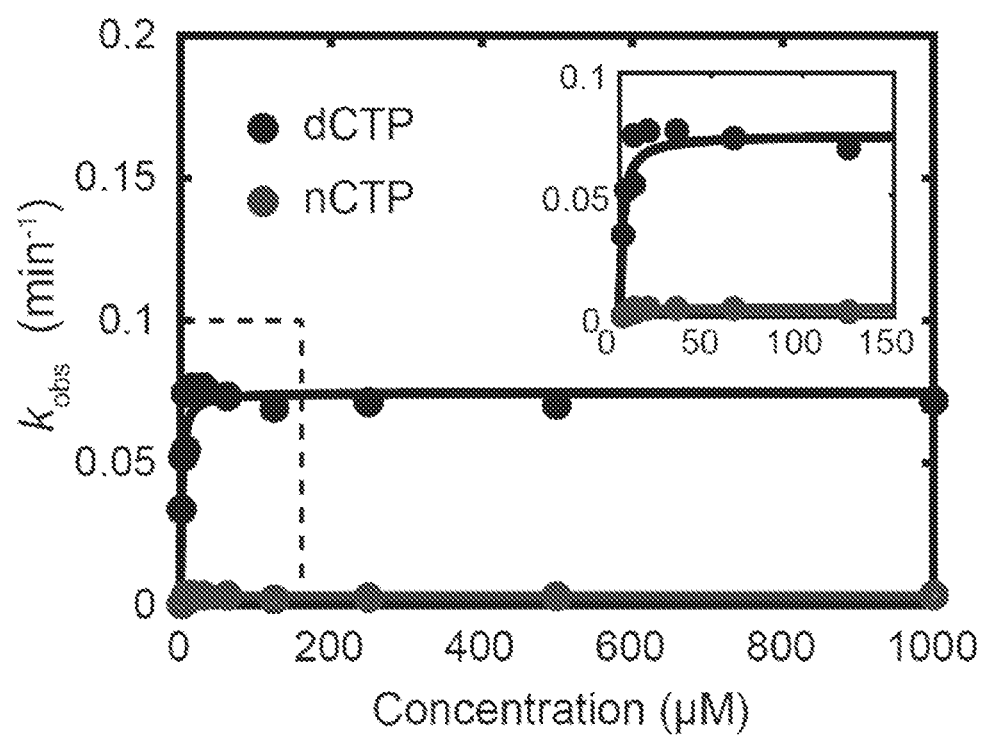
FIG. 3B shows a graph of substrate-dependent rate constants for extension of a 3'-amino primer with varying concentrations of dCTP (black) or nCTP (gray) with 10 mM $CaCl_2$) under pre-steady-state conditions. Parameter estimates in Table 1.
Figure 3C:
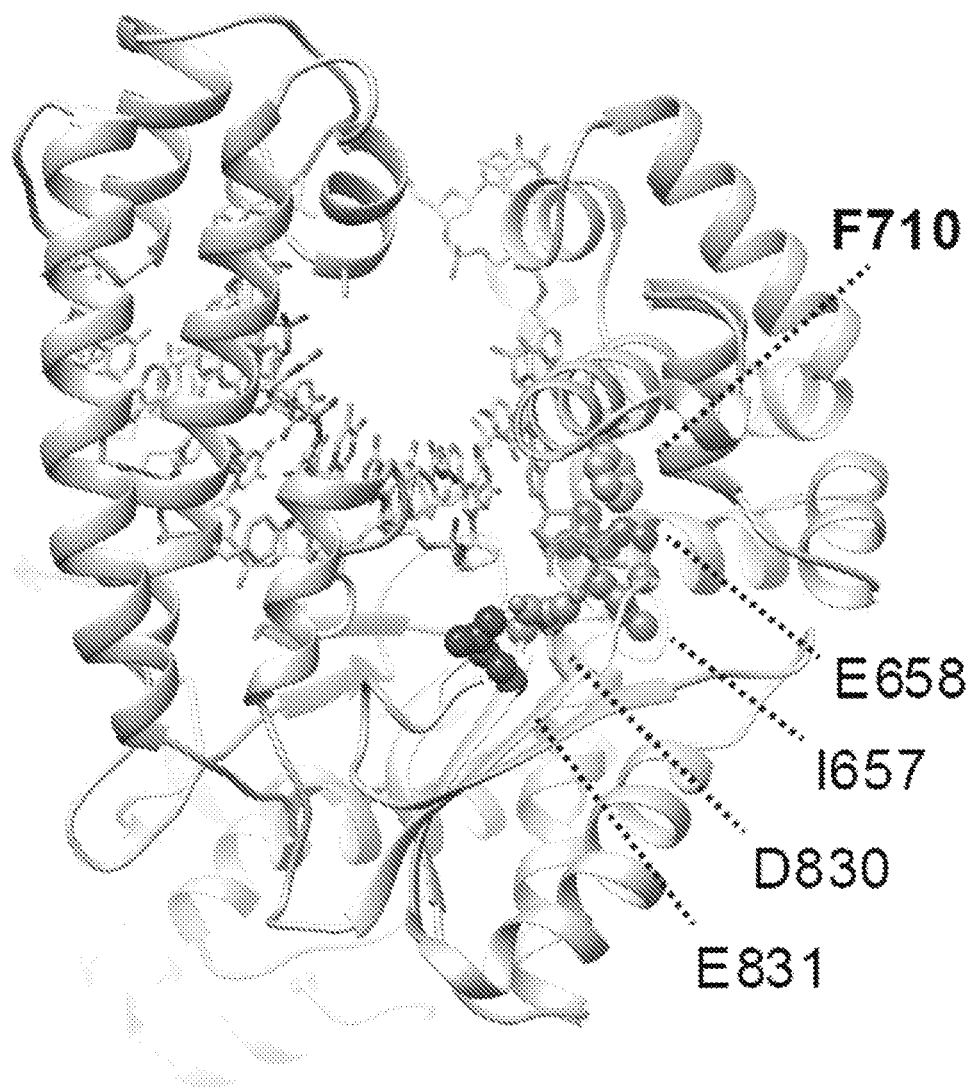
FIG. 3C shows a cartoon of BF closed complex with DNA primer/template and bound substrate (PDB 3EZ5) (Golosov et al., The Mechanism of the Translocation Step in DNA Replication by DNA Polymerase I: A Computer Simulation Analysis. Structure 18, 83-93 (2010)) with mutated active site residues indicated.
Figure 3D:
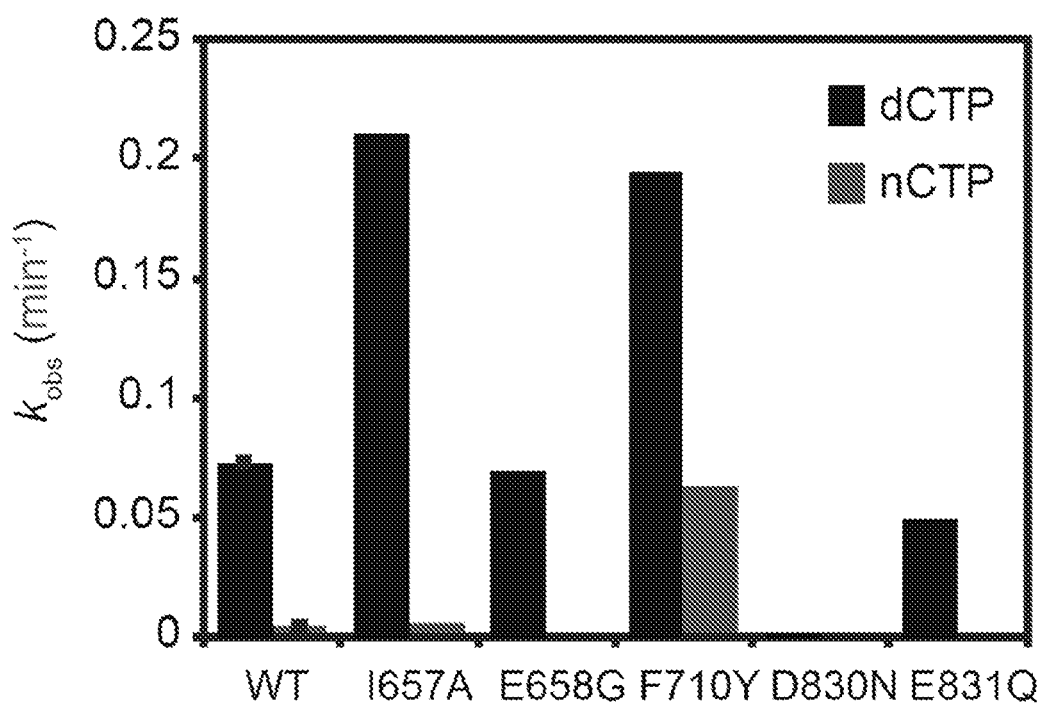
FIG. 3D shows a graph of observed rates of 3'-amino primer extension with either 1 mM dCTP (black) or nCTP (gray) for wild-type (WT) BF and various point mutants.
Figure 5A:
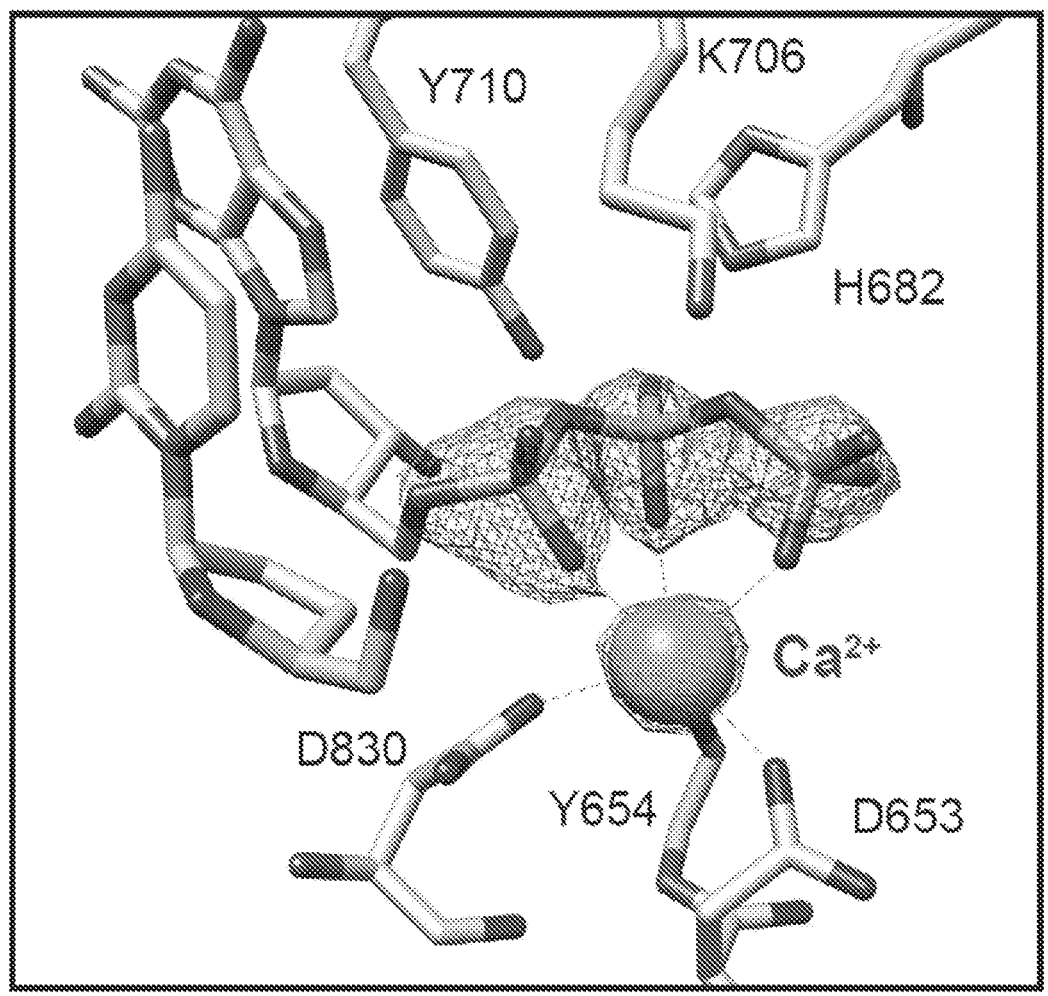
FIG. 5A shows the structure and Fo-Fc omit map (top, gray mesh, 5 σ) for the observed closed reaction complex bound to DNA duplex containing a ddC terminal primer, nGTP substrate, and $Ca^{2+}$.
Figure 5B:
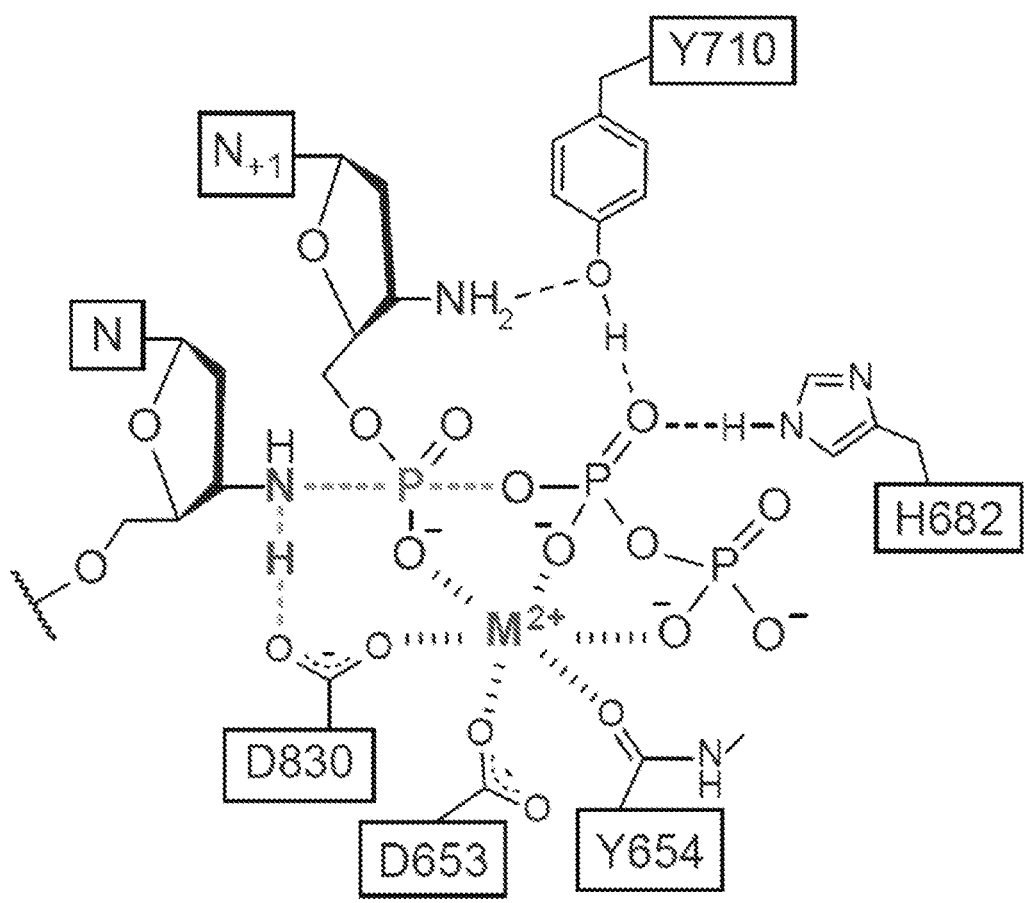
FIG. 5B shows a model of the reaction complex with attacking 3'-amino group (black) of the primer terminus (N) in reaction with the α-phosphate center (gray) of an incoming substrate ($N_{+1}$) and a coordinated metal ion ($M^{2+}$, gray). Interacting residues found in closed complex structures are indicated.

Phosphodiester bonds form the genetic backbone of life on Earth, but phosphoramidate esters do not. It should therefore be unsurprising that highly evolved polymerases are optimized for their wild-type activity and substrate, but it remains notable that 3'-amino nucleotides are not strictly chain terminators. Extension beyond a 3'-amino terminus proceeds with an alternative metal cofactor preference, suggesting mechanistic distinctions in the chemical step between N—P and O—P bond formation. Since the pKa of the protonated 3'-amino group is ~7.5-7.7 as the free nucleoside (Cagri Izgu et al., Synthesis of activated 3'-amino-3'-deoxy-2-thio-thymidine, a superior substrate for the nonenzymatic copying of nucleic acid templates. *Chem. Commun.* 52, 3684-3686 (2016); and Kervio et al., Templating efficiency of naked DNA. *Proc. Natl. Acad. Sci.* 107, 12074-12079 (2010)), consistent with amino functionalities in other glycosylamines (S. Inouye, On the Prediction of pKa Values of Amino Sugars. *Chem. Pharm. Bull.* (Tokyo) 16, 1134-1137 (1968)), the amino nucleophile is expected to be substantially neutral under the reaction conditions. Notably, mutation of two acidic active site residues, which canonically bind a metal ion, activating the nucleophilic 3'-OH in the native O—P reaction, had disparate effects on the N—P reaction. The mutation D830N completely eliminated 3'-amino primer extension, but E831Q did not (FIG. 3D). The kinetics of these mutants, in addition to structural evidence, are more consistent with a role for Asp-830 as a general base than as a metal ligand proximal to the nucleophile (FIG. 5B).

Results described herein demonstrate that this aspartate is likely to play a key role in facilitating proton transfer out of the transition state, in this case without the inner sphere nucleophile-metal ion coordination that is widely understood to activate the nucleophile in the corresponding phosphodiester forming reaction (Steitz et al., A unified polymerase mechanism for nonhomologous DNA and RNA polymerases—Comment/reply. *Sci. Wash.* 266, 2022 (1994)). It is therefore plausible that the distinction in proton transfer between the two reaction mechanisms contributes substantially to the observed kinetic defect. Some additional outer sphere role for divalent ions in the mechanism also cannot be ruled out, since pre-steady-state rates were not saturated at one equivalent of metal ion vs. substrate (FIGS. 2A-2D). $Ca^{2+}$-mediated catalysis of DNA polymerase activity, which was observed in studies described herein, has been previously reported (Irimia et al., Calcium Is a Cofactor of Polymerization but Inhibits Pyrophosphorolysis by the *Sul-* folobus solfataricus DNA Polymerase Dpo4. *Biochemistry* 45, 5949-5956 (2006); and Ralec et al., Calcium-driven DNA synthesis by a high-fidelity DNA polymerase. *Nucleic Acids Res.* 45, 12425-12440 (2017)), but the precise role of $Ca^{2+}$ in the phosphodiester-forming mechanism remains to be elucidated. By co-crystallization, $Ca^{2+}$ bound to the substrate triphosphate moiety in a manner similar to that seen for $Mg^{2+}$ crystallized under similar conditions was observed, but there remains the possibility that structures provided herein do not capture transiently bound metal ions that are nevertheless critical to the reaction mechanism, as has recently been proposed for certain eukaryotic polymerase family members (Gao et al., Capture of a third $Mg^{2+}$ is essential for catalyzing DNA synthesis. *Science* 352, 1334-1337 (2016); and Freudenthal et al., Uncovering the polymerase-induced cytotoxicity of an oxidized nucleotide. *Nature* 517, 635-639 (2015)).

For NP-DNA to participate in any abiogenesis, e.g., a synthetic one undertaken in the laboratory, it would require that this alternative genetic polymer play informational and functional roles in the resulting cell. Given that DNA, RNA, and various XNAs can form folded structures with a broad range of catalytic activities stretching across sequence space, it is reasonable to expect that the sequence space of NP-DNA, too, will contain diverse functions. Although several key aspects of its viability as an alternative genetic polymer remain to be explored, it has long been known that NP-DNA forms stable duplexes with RNA and DNA (Gryaznov et al., Oligodeoxyribonucleotide N3'→P5' Phosphoramidates: synthesis and Hybridization Properties. *J.* *Am. Chem. Soc.* 116, 3143-3144 (1994)), implying its capacity to exchange information. Among alternative nucleic acids known to pair with RNA, only a subset (Kim et al., A model for the emergence of RNA from a prebiotically plausible mixture of ribonucleotides, arabinonucleotides and 2'-deoxynucleotides. *J. Am. Chem. Soc.* 142, 5, 2317-2326 (2020)) are compatible with template-directed nonenzymatic copying chemistry based on phosphorimidazolides. Interestingly, NP-DNA now appears to be compatible with both nonenzymatic phosphorimidazolide and enzymatic triphosphate chemistries. As a result, a genetic transition between backbone linkages is biochemically conceivable with either chemistry.

I. Reaction Components for Producing Oligonucleotides Comprising Phosphoramidate-Linked Nucleotides.

Methods described herein involve the use of a DNA polymerase variant in a pH-buffered aqueous reaction mixture consisting of a divalent metal ion cofactor, nucleotides (e.g., 3'-amino-2',3'-dideoxyribonucleotide 5'-triphosphates (nNTPs), a 3'-amino terminated primer, and a DNA template, to enzymatically produce oligonucleotides comprising phosphoramidate-linked nucleotides.

DNA Polymerase Variants

A DNA polymerase variant, as used herein, refers to a DNA polymerase enzyme comprising a substitution at position F710 (e.g., F710Y) or an equivalent thereof. The DNA polymerase variant can comprise the amino acid sequence of a DNA polymerase from any source, e.g., the amino acid sequence of the DNA polymerase from the thermophilic bacterium *Bacillus stearothermophilus*. It should be understood that the amino acid substitution at position F710 in the DNA polymerase from *B. stearothermophilus* can be incorporated into DNA polymerases from various sources with similar effects on the phosphoramidate bond formation activity of the DNA polymerase. In such instances, the substitution can be at a position other than position 710. For example, as shown in Table 1 below, the substitution equivalent to the substitution at position F710 in the DNA polymerase from *B. stearothermophilus* is at position 762 in the DNA polymerase from *Escherichia coli*.

Non-limiting examples of DNA polymerase variants that can be used to produce oligonucleotides comprising phosphoramidate-linked nucleotides, as provided herein, are provided in Table 1.

TABLE 1

Examples of DNA Polymerases Comprising a Substitution at Position F710 or an equivalent thereof.

| Organism | Gene | Equivalent codon to Bst 710 | Catalytic domain start (C-terminal fragment start) | Accession (Uniprot) | Ref (mutation) |
|---|---|---|---|---|---|
| *Geobacillus stearothermophilus* | POLA | 710 | 469 | P52026, D9N168 | Described herein |
| *Thermus aquaticus* | POLA | 667 | 423 | P19821 | U.S. Pat. No. 5,614,365A |
| *Escherichia coli* | POLA | 762 | 521 | P00582 | U.S. Pat. No. 5,614,365A |
| *Thermus thermophilis* | POLA | 669 | 427 | P52028 | Asakura et al. |
| *Homo sapiens* | POLG | 951 | 738 | P54098 | Lestienne P. |
| Bacteriophage T5 | dpol | 596 | 333 | P19822 | Chatterjee et al. |
| Bacteriophage T7 | gp5 | 526 | 211 | P00581 | U.S. Pat. No. 5,614,365A |

References:
(1) Asakura et al., Cloning, nucleotide sequence, and expression in *Escherichia coli* of DNA polymerase gene (polA) from *Themius thermophilus* HB8. *J. Ferment. Bioeng.* 76, 265-269 (1993).
(2) Lestienne P., Evidence for a direct role of the DNA polymerase gamma in the replication of the human mitochondrial DNA in vitro. *Biochem. Biophys. Res. Commun.* 146 (3), 1146-1153 (1987).
(3) Chatterjee et al., Cloning and overexpression of the gene encoding bacteriophage T5 DNA polymerase. *Gene* 97 (1), 13-19 (1991).

The DNA polymerase variant can comprise a full-length protein or a fragment thereof. In some examples, the DNA polymerase variant comprises the full-length amino acid sequence of the DNA polymerase from *B. stearothermophilus*. In other examples, the DNA polymerase variant comprises a fragment of the full-length amino acid sequence of the DNA polymerase from *B. stearothermophilus*, e.g., a fragment comprising amino acids 298-876, which is provided below as SEQ ID NO: 1.

(SEQ ID NO: 1)
KMAETLADRVTEEMLADKAALVVEVVEENYHDAPIVGIAVVNEHGREEL

RPETALADPQFVAWLGDETKKKSMFDSKRAAVALKWKGIELCGVSFDLL

LAAYLLDPAQGVDDVAAAAKMKQYEAVRPDEAVYGKGAKRAVPDEPVLA

EHLVRKAAAIWELERPFLDELRRNEQDRLLVELEQPLSSILAEMEFAGV

KVDTKRLEQMGKELAEQLGTVEQRIYELAGQEFNINSPKQLGVILFEKL

QLPVLKKTKTGYSTSADVLEKLAPYHEIVENILHYRQLGKLQSTYIEGL

LKVVRPDTKKVHTIFNQALTQTGRLSSTEPNLQNIPIRLEEGRKIRQAF

VPSESDWLIFAADYSQIELRVLAHIAEDDNLMEAFRRDLDIHTKTAMDI

FQVSEDEVTPNMRRQAKAVNFGIVYGISDYGLAQNLNISRKEAAEFIER

YFESFPGVKRYMENIVQEAKQKGYVTTLLHRRRYLPDITSRNFNVRSFA

ERMAMNTPIQGSAADIIKKAMIDLNARLKEERLQAHLLLQVHDELILEA

PKEEMERLCRLVPEVMEQAVTLRVPLKVDYHYGSTWYDAK

The DNA polymerase variant can comprise a mutation in addition to an amino acid substitution at position F710 or an equivalent thereof. Such a mutation can be an insertion, a deletion, a substitution, or a combination thereof. For example, the DNA polymerase variant can comprise an amino acid sequence that is at least 70%, at least 80%, at least 85%, at least 90%, at least 91%, at least 92%, at least 93%, at least 94%, at least 95%, at least 96%, at least 97%, at least 98%, or at least 99% identical to SEQ ID NO: 1, which comprises a substitution at position F710 (e.g., F710Y). In some embodiments, the DNA polymerase variant comprises the amino acid sequence set forth in SEQ ID NO: 1, which comprises a substitution at position F710 (e.g., F710Y).

The DNA polymerase variant to be used in methods described herein can be prepared by any known method. The DNA polymerase variant can be added to a reaction mixture as a recombinant protein and/or as a cell lysate from cells that express the DNA polymerase variant. In some embodiments, the DNA polymerase variant can comprise a fusion protein or a tagged protein (e.g., a His$_6$-tagged DNA polymerase variant).

Divalent Metal Ion Cofactors

A divalent metal ion cofactor enhances the catalytic efficiency of the DNA polymerase variant in synthesis of phosphoramidate-linked nucleotides. Non-limiting examples of divalent metal ion cofactors include $Ba^{2+}$, $Sr^{2+}$, $Ca^{2+}$, $Mg^{2+}$, $Mn^{2+}$, $Co^{2+}$, and $Zn^{2+}$. In some embodiments, the divalent metal ion cofactor is $Ca^{2+}$.

Nucleotides

Methods described herein involve polymerization of nucleotides via phosphoramidate linkages using a DNA polymerase variant. Any suitable nucleotide can be used in methods described herein. Nucleotides can be modified or unmodified. Nucleotides can be naturally occurring or synthetic.

For example, the nucleotide can be a 3'-amino-2',3'-dideoxyribonucleotide 5'-triphosphate (nNTP). Examples of 3'-amino-2',3'-dideoxyribonucleotide 5'-triphosphate (nNTPs) include 3'-amino-2',3'-dideoxyadenosine 5'-triphosphate (nATP), 3'-amino-2',3'-dideoxycytidine 5'-triphosphate (nCTP), 3'-amino-2',3'-dideoxyguanosine 5'-triphosphate (nGTP), 3'-amino-2',3'-deoxythymidine 5'-triphosphate (nTTP).

In another example, the nucleotide can be a deoxynucleoside triphosphate (dNTP). Examples of deoxynucleoside triphosphates (dNTPs) include 2'-deoxyadenosine 5'-triphosphate (dATP), 2'-deoxycytidine 5'-triphosphate (dCTP), 2'-deoxyguanosine 5'-triphosphate (dGTP), 2'-deoxythymidine 5'-triphosphate (dTTP).

In yet another example, the nucleotide can be a nucleoside triphosphate (NTP). Examples of nucleoside triphosphates (NTPs) include adenosine 5'-triphosphate (ATP), cytidine 5'-triphosphate (CTP), guanosine 5'-triphosphate (GTP), and uridine 5'-triphosphate (UTP).

Nucleotides and oligonucleotides disclosed herein can comprise any suitable modified nucleotide such as those known in the art. Modified nucleotides include, but are not limited to, nucleotides comprising a backbone modification, a base modification, and/or a sugar modification. Non-limiting examples of backbone modifications include phosphorothioate modifications, methylphosphonate modification, phosphoramidate modifications, and locked nucleic acid (LNA) backbone modifications. Non-limiting examples of base modifications include substituted purines and pyrimidines. Non-limiting examples of sugar modifications include 2'-O-alkylated or 2'-fluorinated ribose and arabinose. Other such modifications are well known to those of skill in the art.

3'-Amino Terminated Primers

Methods described herein involve extension of a 3'-amino terminated primer by a DNA polymerase variant to produce oligonucleotides comprising phosphoramidate-linked nucleotides. The 3'-amino terminated primer can comprise ribonucleotides, deoxyribonucleotides, or a combination thereof.

Nucleotides in the 3'-amino terminated primer can be linked by a single type of linkage or by different types of linkages. As such, the 3'-amino terminated primer can be referred to as comprising one type of linkage or mixed types of linkages. For example, when the 3'-amino terminated primer comprises one type of linkage, the 3'-amino terminated primer can comprise phosphodiester-linked nucleotides or phosphoramidate-linked nucleotides. In another example, when the 3'-amino terminated primer comprises multiple types of linkages, the 3'-amino terminated primer can comprise phosphodiester-linked nucleotides and phosphoramidate-linked nucleotides.

Any length 3'-amino terminated primer can be used in methods described herein. In some embodiments, the 3'-amino terminated primer is 5 to 200 nucleotides in length. In some embodiments, the is 3'-amino terminated primer is 25 to 200 nucleotides, 50 to 200 nucleotides, 75 to 200 nucleotides, 100 to 200 nucleotides, 125 to 200 nucleotides, 150 to 200 nucleotides, 175 to 200 nucleotides, 5 to 175 nucleotides, 5 to 150 nucleotides, 5 to 125 nucleotides, 5 to 100 nucleotides, 5 to 75 nucleotides, 5 to 50 nucleotides, or 5 to 25 nucleotides in length.

In some embodiments, the 3'-amino terminated primer is 10 to 50 nucleotides, 15 to 50 nucleotides, 20 to 50 nucleotides, 25 to 50 nucleotides, 30 to 50 nucleotides, 35 to 50 nucleotides, 40 to 50 nucleotides, 45 to 50 nucleotides, 5 to 45 nucleotides, 5 to 40 nucleotides, 5 to 35 nucleotides, 5 to 30 nucleotides, 5 to 25 nucleotides, 5 to 20 nucleotides, 5 to 15 nucleotides, or 5 to 10 nucleotides in length.

The 3'-amino terminated primer can comprise any number of consecutive phosphoramidate-linked nucleotides. In some embodiments, the 3'-amino terminated primer comprises at least 5, at least 10, at least 15, at least 20, at least 25, at least 30, at least 35, at least 40, at least 45, or at least 50 consecutive phosphoramidate-linked nucleotides. In some embodiments, each nucleotide in the 3'-amino terminated primer is phosphoramidate-linked.

The 3'-amino group of the 3'-amino terminated primer can be incorporated into a ribonucleotide or a deoxyribonucleotide. Accordingly, the 3'-amino terminated primer can comprise a 3'-amino terminal ribonucleotide or a 3'-amino terminal deoxyribonucleotide.

In some examples, the 3'-amino residue is incorporated into ribonucleotide, and the 3'-amino terminal ribonucleotide can be selected from the group consisting of 3'-amino-adenosine, 3'-amino-guanosine, 3'-amino-cytidine, and 3'-amino-uridine.

In other examples, the 3'-amino residue is incorporated into deoxyribonucleotide, and 3'-amino terminal dideoxynucleotide selected from the group consisting of 3'-amino-2',3'-dideoxyadenosine (nA), 3'-amino-2',3'-dideoxythymidine (nT), 3'-amino-2',3'-dideoxycytidine (nC), 3'-amino-2',3'-dideoxyguanosine (nG), or 3'-amino-2',3'-dideoxyuridine (nU).

The 3'-amino terminated primer can be unlabeled or labeled. The 3'-amino terminated primer can be labeled with any suitable label, which can be any suitable chemical or molecule (e.g., a non-nucleotide molecule). Examples of labels include, but are not limited to, fluorescent dyes (e.g., fluorophores), affinity tags (e.g., biotin), luminescent agents, electron-dense reagents, enzymes (e.g., luciferase), isotopes (e.g., $^{32}P$), haptens, and proteins. The 3'-amino terminated primer can be labeled using any method known in the art (e.g., click chemistry).

In some embodiments, the 3'-amino terminated primer comprises a detectable label, which refers to any molecule that is capable of releasing a detectable signal, either directly or indirectly. Any detectable label known in the art (e.g., a fluorescent label or a radioactive label) can be incorporated into the 3'-amino terminated primer. For example, the 3'-amino terminated primer can comprise a detectable label such as a fluorescent label (e.g., fluorescein, Cy3). The detectable label can be attached to any nucleotide in the 3'-amino terminated primer. In some embodiments, the 3'-amino terminated primer comprises a 5'-detectable label.

DNA Templates

Methods provided herein produce oligonucleotides comprising phosphoramidate-linked nucleotides in a DNA template-directed manner. The DNA template for use in such methods comprises a sequence complementary to a 3'-amino terminated primer and a nucleic acid sequence of interest. In some embodiments, the DNA template comprises, from 3' to 5', a sequence complementary to a 3'-amino terminated primer and a nucleic acid sequence of interest.

Any suitable nucleic acid sequence of interest can be used in a DNA template described herein. The nucleic acid sequence of interest can vary depending on the downstream use of the oligonucleotide thus produced. For example, when the oligonucleotide can be used in gene editing, the nucleic acid sequence can be complementary to the target gene.

DNA templates for use in methods described herein can be linear, e.g., linear DNA templates generated by polymerase chain reaction (PCR), chemical synthesis, or other means known in the art. In some embodiments, the template can be circular, e.g., provided in a vector such as a plasmid.

The DNA template can comprise one type of linkage or multiple types of linkages. For example, when the DNA template comprises one type of linkage, the DNA template can comprise phosphodiester-linked nucleotides or phosphoramidate-linked nucleotides. In another example, when the DNA template comprises multiple types of linkages, the DNA template can comprise phosphodiester-linked nucleotides and phosphoramidate-linked nucleotides.

II. Methods for Producing Oligonucleotides Comprising Phosphoramidate-Linked Nucleotides.

Aspects of the present disclosure provide methods for producing oligonucleotides comprising phosphoramidate-linked (NP-linked) nucleotides. Such methods involve incubating a sample comprising a DNA polymerase variant, a divalent metal ion cofactor, 2',3'-dideoxyribonucleotide 5'-triphosphates (nNTPs), a 3'-amino terminated primer, and a DNA template in a pH-buffered aqueous solution, each of which are disclosed herein.

To produce an oligonucleotide comprising phosphoramidate-linked nucleotides, a sample is incubated under conditions sufficient for the DNA polymerase variant to produce the oligonucleotide comprising NP-linked nucleotides. Such conditions include, but are not limited to, incubating the sample for a suitable period of time at a suitable temperature and a suitable pH.

Methods described herein encompass incubating a sample for any period of time sufficient for the DNA polymerase variant to produce an oligonucleotide comprising phosphoramidate-linked nucleotides. In some embodiments, the sample is incubated for 0.5 to 48 hours. In some embodiments, the sample is incubated for 0.5 to 48 hours, 1 to 48 hours, 2 to 48 hours, 3 to 48 hours, 4 to 48 hours, 5 to 48 hours, 6 to 48 hours, 12 to 48 hours, 24 to 48 hours, 36 to 48 hours, 0.5 to 36 hours, 0.5 to 24 hours, 0.5 to 12 hours, 0.5 to 6 hours, 0.5 to 5 hours, 0.5 to 4 hours, 0.5 to 3 hours, 0.5 to 2 hours, or 0.5 to 1 hours. In some embodiments, the sample is incubated for 0.5 hour, 1 hour, 2 hours, 3 hours, 4 hours, 5 hours, 6 hours, 12 hours, 24 hours, 36 hours, 48 hours, or more.

Methods described herein encompass incubating a sample at any temperature sufficient for the DNA polymerase variant to produce an oligonucleotide comprising phosphoramidate-linked nucleotides.

In some embodiments, the sample is incubated at a temperature of 25 to 37° C., e.g., at a temperature of 25° C., 26° C., 27° C., 28° C., 29° C., 30° C., 31° C., 32° C., 33° C., 34° C., 35° C., 36° C., or 37° C. In some embodiments, the sample is incubated at a temperature of 37° C.

In some embodiments, the sample is incubated at a temperature of 50 to 65° C., e.g., at a temperature of 50° C., 51° C., 52° C., 53° C., 54° C., 55° C., 55° C., 57° C., 58° C., 59° C., 60° C., 61° C., 62° C., 63° C., 64° C., or 65° C. In some embodiments, the sample is incubated at a temperature of 55° C.

Methods described herein encompass incubating a sample at any pH sufficient for the DNA polymerase variant to produce an oligonucleotide comprising phosphoramidate-linked nucleotides. In some embodiments, the sample is incubated at a pH of 7 to 10, 8 to 10, 9 to 10, 7 to 9, or 7 to 8. In some embodiments, the sample is incubated at a pH of 8.6 to 9.2, 8.7 to 9.2, 8.8 to 9.2, 8.9 to 9.2, 9.0 to 9.2, 9.1 to 9.2, 8.6 to 9.1, 8.6 to 9.0, 8.6 to 8.9, 8.6 to 8.8, or 8.6 to 8.7. In some embodiments, the sample is incubated at a pH of 8.8.

In some embodiments, buffer is added to a sample to achieve a particular pH and/or salt concentration. Examples of buffers include, but are not limited to, phosphate buffer, Tris buffer, MOPS buffer, HEPES buffer, EPPS buffer, and POPSO buffer.

Any suitable divalent metal ion cofactor can be used in methods described herein. Accordingly, the sample can comprise any suitable divalent metal ion cofactor sufficient for the DNA polymerase variant to produce an oligonucleotide comprising phosphoramidate-linked nucleotides. In some embodiments, the sample comprises $Ba^{2+}$, $Sr^{2+}$, $Ca^{2+}$, Mg$^{2+}$, Mn$^{2+}$, Co$^{2+}$, Zn$^{2+}$, or a combination thereof. In some embodiments, the sample comprises Ca$^{2+}$.

The sample can comprise any suitable concentration of a divalent metal ion cofactor. In some embodiments, the sample comprises a divalent metal ion cofactor at a concentration of 1 to 50 mM. In some embodiments, the sample comprises a divalent metal ion cofactor at a concentration of 5 to 50 mM, 10 to 50 mM, 15 to 50 mM, 20 to 50 mM, 25 to 50 mM, 30 to 50 mM, 35 to 50 mM, 40 to 50 mM, 45 to 50 mM, 5 to 45 mM, 5 to 40 mM, 5 to 35 mM, 5 to 30 mM, 5 to 25 mM, 5 to 20 mM, 5 to 15 mM, or 5 to 10 mM.

Any DNA polymerase variant, such as those described herein, can be used in methods provided herein. Accordingly, the sample comprises any DNA polymerase variant described herein. In some embodiments, the sample can comprise a DNA polymerase variant, which comprises an amino acid sequence that is at least 70%, 80%, 90%, or 95% identical to SEQ ID NO: 1. In some embodiments, the sample comprises a DNA polymerase variant set forth in SEQ ID NO: 1.

Methods described herein encompass incubating a sample comprising any amount of a DNA polymerase variant sufficient for the DNA polymerase variant to produce an oligonucleotide comprising phosphoramidate-linked nucleotides. For example, the sample can comprise the DNA polymerase variant at a concentration of 0.1 to 10 µM (e.g., at a concentration of 0.1 µM, 0.5 µM, 1 µM, 5 µM, or 10 µM).

DNA polymerase variants in any suitable form can be used in methods described herein. For example, the DNA polymerase variant can be provided as a cell lysate from cells that express the DNA polymerase variant. In another example, the DNA polymerase variant can be provided as a recombinant protein purified from cells that express the DNA polymerase variant. In yet another example, the DNA polymerase variant can be provided as nucleic acids encoding the DNA polymerase variant.

Methods described herein involve template-directed polymerization of 3'-amino-2',3'-dideoxyribonucleoside 5'-triphosphates (nNTPs) to produce oligonucleotides comprising phosphoramidate-linked nucleotides. Accordingly, methods described herein comprise incubating a sample comprising nNTPs. In some embodiments, the sample comprises 3'-amino-2',3'-dideoxyadenosine 5'-triphosphate (nATP), 3'-amino-2',3'-dideoxycytidine 5'-triphosphate (nCTP), 3'-amino-2',3'-dideoxyguanosine 5'-triphosphate (nGTP), 3'-amino-2',3'-deoxythymidine 5'-triphosphate (nTTP), or a combination thereof.

Methods described herein can produce oligonucleotides comprising mixed linkages (e.g., phosphoramidate-linked nucleotides and phosphodiester-linked nucleotides) using nucleotides comprising a 3'-hydroxyl group and lacking a 3'-amino modification. For example, in such methods, the sample can comprise nNTPs and deoxynucleoside triphosphates (dNTPs). In some embodiments, the sample can comprise 2'-deoxyadenosine 5'-triphosphate (dATP), 2'-deoxycytidine 5'-triphosphate (dCTP), 2'-deoxyguanosine 5'-triphosphate (dGTP), 2'-deoxythymidine 5'-triphosphate (dTTP), or a combination thereof. In another example, the sample can comprise nNTPs and nucleoside triphosphates (NTP). In some embodiments, the sample can comprise adenosine 5'-triphosphate (ATP), cytidine 5'-triphosphate (CTP), guanosine 5'-triphosphate (GTP), and uridine 5'-triphosphate (UTP), or a combination thereof.

Any suitable 3'-amino terminated primer, such as those described herein, can be used in methods provided herein. Accordingly, methods described herein comprise incubating a sample comprising any 3'-amino terminated primer. In some embodiments, the sample can comprise a 3'-amino terminated primer comprising ribonucleotides and/or deoxyribonucleotides. In some embodiments, the sample can comprise a 3'-amino terminated primer comprising a 5'-detectable label.

Any suitable amount of a 3'-amino terminated primer can be used in methods described herein. For example, the sample can comprise a 3'-amino terminated primer at a concentration of 0.1 to 10 µM. In some embodiments, the sample can comprise a 3'-amino terminated primer at a concentration of 0.25 to 10 µM, 0.5 to 10 µM, 1 to 10 µM, 2.5 to 10 µM, 5 to 10 µM, 7.5 to 10 µM, 0.1 to 7.5 µM, 0.1 to 5 µM, 0.1 to 2.5 µM, 0.1 to 1 µM, 0.1 to 0.5 µM, or 0.1 to 0.25 µM.

Any suitable DNA template, such as those described herein, can be used in methods provided herein. Accordingly, methods described herein comprise incubating a sample comprising a DNA template. In some embodiments, the sample comprises a DNA template comprising, from 3' to 5', a sequence complementary to a 3'-amino terminated primer and a nucleic acid sequence of interest.

Any suitable amount of a DNA template can be used in methods described herein. For example, the sample can comprise a DNA template at a concentration of 0.1 to 10 µM. In some embodiments, the sample can comprise a DNA template at a concentration of 0.25 to 10 µM, 0.5 to 10 µM, 1 to 10 µM, 2.5 to 10 µM, 5 to 10 µM, 7.5 to 10 µM, 0.1 to 7.5 µM, 0.1 to 5 µM, 0.1 to 2.5 µM, 0.1 to 1 µM, 0.1 to 0.5 µM, or 0.1 to 0.25 µM.

Methods described herein encompass incubating a sample of any suitable volume. For example, the sample can comprise a volume of 0.1 mL, 1 mL, 100 mL, 1 L, or more. Depending on the size of the sample, the amount of the oligonucleotide produced according to methods described herein can be 1 ng to 1 mg or more (e.g., 1 ng, 10 ng, 100 ng, 1 µg, 10 µg, 100 µg, 1 mg, or more).

III. Oligonucleotides Comprising Phosphoramidate-Linked Nucleotides.

Aspects of the present disclosure provide an oligonucleotide comprising phosphoramidate-linked (NP-linked) nucleotides produced according to methods described herein.

Oligonucleotides produced according to methods described herein can be various lengths. For example, the oligonucleotide can be at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250 or more nucleotides in length.

In some embodiments, the oligonucleotide is 25 to 250 nucleotides in length. In some embodiments, the oligonucleotide is 25 to 225 nucleotides, 25 to 200 nucleotides, 25 to 175 nucleotides, 25 to 150 nucleotides, 25 to 125 nucleotides, 25 to 100 nucleotides, 25 to 75 nucleotides, 25 to 50 nucleotides, 50 to 250 nucleotides, 75 to 250 nucleotides, 100 to 250 nucleotides, 125 to 250 nucleotides, 150 to 250 nucleotides, 175 to 250 nucleotides, 200 to 250 nucleotides, or 225 to 250 nucleotides.

In some embodiments, the oligonucleotide is 25 to 150 nucleotides in length. In some embodiments, the oligonucleotide is 25 to 125 nucleotides, 25 to 100 nucleotides, 25 to 75 nucleotides, 25 to 50 nucleotides, 50 to 150 nucleotides, 75 to 150 nucleotides, 100 to 150 nucleotides, or 125 to 150 nucleotides.

In some embodiments, the oligonucleotide is 25 to 100 nucleotides in length. In some embodiments, the oligonucleotide is 25 to 95 nucleotides, 25 to 90 nucleotides, 25 to 85 nucleotides, 25 to 80 nucleotides, 25 to 75 nucleotides, 25 to 70 nucleotides, 25 to 65 nucleotides, 25 to 60 nucleotides, 25 to 55 nucleotides, 25 to 50 nucleotides, 25 to 45 nucleotides, 25 to 40 nucleotides, 25 to 35 nucleotides, or 25 to 30 nucleotides in length.

In some embodiments, the oligonucleotide is 30 to 100 nucleotides, 35 to 100 nucleotides, 40 to 100 nucleotides, 45 to 100 nucleotides, 50 to 100 nucleotides, 55 to 100 nucleotides, 60 to 100 nucleotides, 65 to 100 nucleotides, 70 to 100 nucleotides, 75 to 100 nucleotides, 80 to 100 nucleotides, 85 to 100 nucleotides, 90 to 100 nucleotides, or 95 to 100 nucleotides in length.

Nucleotides in the oligonucleotide produced according to methods described herein can be ribonucleotides and/or deoxyribonucleotides. An oligonucleotide comprising ribonucleotides and deoxyribonucleotides can be referred to as a mixed or chimeric oligonucleotide. In general, a mixed oligonucleotide refers to an oligonucleotide comprising a mix of structural components such as a mix of nucleotides (e.g., ribonucleotides and deoxyribonucleotides) and/or an oligonucleotide comprising two or more kinds of backbone or internucleotide linkages (e.g., phosphoramidate linkages and phosphodiester linkages).

Nucleotides in the oligonucleotide can comprise any modification known in the art such as those described herein. In some embodiments, one or more nucleotides in the oligonucleotide can comprise a backbone modification, which can reduce nuclease-mediated degradation of the oligonucleotide. For example, one or more of the nucleotides in the oligonucleotide can comprise a locked nucleic acid (LNA) modification in which the nucleotide comprises a modified sugar residue with an additional 2'-C,4'-C-oxymethylene linker that confines the ribose ring to the 3'-endo conformation.

Alternatively, or in addition to, one or more nucleotides in the oligonucleotide can comprise a modification of the base or the sugar moieties. For example, one or more nucleotides in the oligonucleotide can comprise arabinose instead of ribose. In another example, one or more nucleotides in the oligonucleotide can comprise a substituted base such as a substituted pyrimidine (e.g., 5-methylcytosine) or isomer (e.g., pseudouridine).

At least a portion of the nucleotides in the oligonucleotide are linked by phosphoramidate linkages. In some examples, each nucleotide in the oligonucleotide is phosphoramidate-linked. In other examples, a portion of the nucleotides in the oligonucleotide can be phosphoramidate-linked and a portion of the nucleotides in the oligonucleotide can be linked via another type of linkage (e.g., phosphodiester linkage, phosphorothioate linkage). In such instances, the oligonucleotide can be referred to as having mixed linkages.

In some embodiments, the oligonucleotide comprises a plurality of phosphoramidate-linked nucleotides. In some embodiments, the oligonucleotide comprises at least 5, at least 10, at least 15, at least 20, at least 25, at least 30, at least 35, at least 40, at least 50, at least 60, at least 70, at least 80, at least 90, at least 100, or more consecutive phosphoramidate-linked nucleotides. In some embodiments, each nucleotide in the oligonucleotide is phosphoramidate-linked.

The oligonucleotide produced by methods described herein can be any form. Examples include, but are not limited to, aptamers, antisense oligonucleotides (e.g., antisense RNA, antisense DNA, DNA/RNA heteroduplex oligonucleotides, splice-switching oligonucleotides), guide RNA (gRNA), messenger RNA (mRNA), micro RNA (miRNA), small interfering RNA (siRNA), and single-stranded DNA.

In some instances, two different oligonucleotides having complementary sequences can be produced according to methods described herein, and the resulting oligonucleotides can be used to form a double-stranded oligonucleotide.

IV. Applications of Oligonucleotides Comprising Phosphoramidate-Linked Nucleotides.

Any of the oligonucleotides described herein can be used in any suitable application in which oligonucleotides are utilized. One of ordinary skill in the art will readily recognize that the present disclosure is not limited to particular use but is applicable to any situation in which the use of oligonucleotides is desirable. For example, oligonucleotides disclosed herein can be used in microarray technologies, fluorescence in situ hybridization (FISH) technologies, antisense applications, sequencing, and gene editing technologies (e.g., CRISPR-Cas9 gene editing technologies). In another example, oligonucleotides disclosed herein can be used as agents for modulating a cellular process and/or a cellular machinery, including but not limited to, transcription, translation, immune responses, and epigenetics. Accordingly, any of the oligonucleotides disclosed herein can be used for therapeutic, diagnostic, agricultural, and/or research purposes.

In such instances, an oligonucleotide described herein can comprise a sufficient degree of complementarity to a target element (e.g., a target gene, target mRNA, target regulatory element) to reduce expression of the target element or other activity at the target element. A sufficient degree of complementarity ensures that the oligonucleotide specifically binds to the target sequence and avoids non-specific binding of the oligonucleotide to non-target sequences under conditions in which specific binding is desired, e.g., under physiological conditions in the case of in vivo assays or therapeutic treatment, or in the case of in vitro assays, under conditions in which the assays are performed.

Any method known in the art can be used to deliver any of the oligonucleotides described herein to a cell, a tissue, or an organism. For example, the oligonucleotide can be delivered by injection (e.g., microinjection), electroporation, and liposome-mediated transfection.

When used in a therapeutic application, an oligonucleotide described herein can be administered to a subject. In such instances, the oligonucleotide can be mixed with a pharmaceutically acceptable carrier (excipient) to form a pharmaceutical composition for use in treating a target disease. "Acceptable" means that the carrier must be compatible with the oligonucleotide and not deleterious to the subject to be treated. Pharmaceutically acceptable excipients (carriers) including buffers are well known in the art. See, e.g., Remington: The Science and Practice of Pharmacy $20^{th}$ Ed. (2000) Lippincott Williams and Wilkins, Ed. K. E. Hoover.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described may be more fully understood, the following examples are set forth. The examples described in this application are offered to illustrate the methods and compositions provided herein and are not to be construed in any way as limiting their scope.

Materials and Methods

The following materials and methods were used in the Examples set forth herein.

Materials. 3'-Deoxyribonucleotide 5'-triphosphates were obtained from New England Biolabs. 3'-Amino-2',3'-dideoxyribonucleotide 5'-triphosphates were obtained from Trilink Biotechnologies. DNA oligonucleotides were purchased from IDT. Oligonucleotides incorporating a 3'-amino residue were synthesized and purified by standard methods, using phosphoramidites obtained from Chemgenes or as recently reported (Lelyveld et al., DNA polymerase activity on synthetic N3'→P5' phosphoramidate DNA templates. *Nucleic Acids Res.* 47, 8941-8949 (2019)) and using reagents purchased from Glen Research on an Expedite 8909 synthesizer. Premixed reagent solutions for crystallization were purchased from Hampton Research. Recombinant lysozyme and Bugbuster lysis reagent were purchased from EMD. Ni-NTA Superflow affinity resin was purchased from Qiagen. All other buffers and reagents were prepared from high purity chemicals obtained from Sigma Sigma-Aldrich, using chemicals with trace metals analysis where available. Competent cells were obtained from New England Biolabs.

Recombinant protein preparation. A bacterial expression plasmid carrying the codon-optimized open reading frame for the DNA polymerase I large fragment (amino acids 297-877) from Bst (BF) fused at its N-terminus to a His6 tag and an HRV 3C protease signal sequence, was produced by standard methods. BF expression was placed under the control of a lacO-regulated T5 promoter based on the expression system from pQE-30. The plasmid backbone carries a kanamycin resistance cassette and lacI derived from pET-28. The resulting plasmid, pVSL5, was used to transform DH5a cells and selected on LB plates containing kanamycin. For protein expression, starter cultures were inoculated from a single colony and grown overnight in LB+1% glucose and kanamycin at 30 μg/mL at 30° C. The overnight culture was then inoculated 1:100 into a shake flask containing LB and antibiotic, and the culture was expanded at 37° C. with 225 rpm shaking (e.g., with 0.5 L medium in a 2 L flask). When the optical density at 600 nm reached ~0.6-0.8 in a 1 cm path length cuvette, expression of BF was induced by addition of 1 mM IPTG, and induction was allowed to proceed for 2 hr at 37° C. Cells were harvested by centrifugation at 4° C., and the resulting cell pellet was typically stored at ~80° C. prior to purification. Thawed pellets were lysed in 1× BugBuster, adjusted to pH ~8.5 by addition of KOH, containing 0.001×EDTA-free Protease Inhibitor Cocktail Set III (Calbiochem) and lysozyme. The lysate was heat treated in a water bath at 50° C. for 20 min, and its viscosity was reduced by probe sonication at 0° C. The lysate was then clarified by centrifugation at 16000 g for 30 min at 4° C. The polyhistidine-tagged protein was purified by batch binding to Ni-NTA beads that had been pre-equilibrated in 1× BugBuster. The resin was washed with 1 column volume (CV) of BugBuster, followed by 10 CV of 20 mM sodium phosphate, pH 7.6, 0.5 M NaCl, 12.5 mM imidazole. An additional wash with a higher salt buffer, otherwise as above except containing 1 M NaCl, reduced nonspecific binding. The protein was eluted with 20 mM sodium phosphate, pH 7.6, 0.5 M NaCl, 250 mM imidazole, and DTT was added to the resulting fractions up to 2 mM. The protein was concentrated using centrifugal MWCO filtration devices (Millipore), desalted into a 2× storage buffer using a disposable size exclusion column (NAP25, GE Amersham) following the manufacturer's protocol, and then reconcentrated. The 2× storage buffer contained 20 mM Tris-Cl, pH 7.6, 100 mM KCl, 2 mM DTT, 0.2 mM EDTA, and 0.2% Triton X-100. The resulting protein preparation was diluted 2-fold by gradual addition of 1 volume of glycerol, then stored at −30° C. To prepare protein for crystallization, elution fractions from the Ni-NTA resin were diluted 1:1 by addition of the 2× storage buffer without Triton X-100, followed by HRV 3C protease for cleavage of the affinity tag. The cleavage reaction proceeded overnight at 4° C., and the His-tagged protease and cleaved peptide were removed by passing the solution over Ni-NTA resin, followed by concentration and desalting into 1× storage buffer, as above except omitting the nonionic surfactant.

Co-crystallizations. Preparations of the wild type or D598A/F710Y double-mutant BF were concentrated to 20 mg/mL. The mutation D598A reportedly disrupts a crystal contact that otherwise precludes crystallization of the closed conformation of the fingers domain (Johnson et al., Processive DNA synthesis observed in a polymerase crystal suggests a mechanism for the prevention of frameshift mutations. *Proc. Natl. Acad. Sci.* 100, 3895-3900 (2003)). A DNA primer, containing either a 3' terminal 2',3'-dideoxycytidine (5'-GCGATCAGddC (SEQ ID NO: 2)) or 3'-amino-2',3'-dideoxycytidine (5'-GCGATCAGnC (SEQ ID NO: 2)) residue, was prepared and annealed with a partially complementary DNA template oligonucleotide (5'-ACACGCTGATCGCA (SEQ ID NO: 3)) in the presence of either dGTP, nGTP, or dGpNHpp, as indicated. The final concentrations of primer/template duplex and substrate were 0.25 mM and 3 mM, respectively. Protein was added to a final concentration of 10 mg/mL and allowed to complex by incubating at 37° C. for ~10-20 min or overnight at 4° C. To obtain crystals of the substrate-bound closed conformation, mixtures of the D598A/F710Y double mutant protein containing substrate, primer, and template were screened by mixing 1:1 with crystallization reagent solutions containing 0.1 M Na-MES pH 5.4 or 5.8 buffer, 2 M ammonium sulfate, 2.5% or 5% (v/v) (+/−)-2-methyl-2,4-pentanediol, and 10 mM of $MgSO_4$, $CaCl_2$, $MnSO_4$, or $CoCl_2$. Structures in the closed conformation with ordered substrate and metal ion were obtained only with calcium, manganese, or cobalt ions. Crystallization proceeded by the sitting-drop vapor diffusion method. Crystals typically appeared within 2-4 days at 18° C. Prior to mounting and freezing, crystals were soaked in a solution of the same reagent mix as for crystallization, except where the buffer was replaced with 0.1 M Na-EPPS, pH 8.8, and the substrate concentration was 0.5 mM. Soak time was screened from ~2 min-90 min at 20° C. For the closed conformation structure containing $Ca^{2+}$ and dGpNHpp (6UR9), the crystal was formed at pH 5.4 with 2.5 MPD, and the soak time at pH 8.8 was ~20 min. For the closed conformation structure containing $Mn^{2+}$ and nGTP (6US5), the crystal was formed at pH 5.4 with 5% MPD, and the soak time was ~5 min at pH 8.8. Crystals of the wild-type BF complex in the open conformation were prepared similarly, except using 8 mM dGTP and 20 mM $MgCl_2$ in the protein complex mix, and these crystals were mounted and frozen directly from the mother liquor without any additional soaking. No ordered density corresponding dGTP or $Mg^{2+}$ were observed in these open conformation wild-type structures. The pre-reaction open structure (0 Complex, 6UR4) was crystallized by mixing the protein complex solution 1:1 with 60% v/v Tacsimate, pH 7.0. Tascimate (Hampton Research) is a reagent mix containing 1 M malonic acid, 0.15 M ammonium citrate tribasic, 0.07 M Succinic acid, 0.18 M DL-malic acid, 0.24 M sodium acetate trihydrate, 0.3 M sodium formate, 0.1 M ammonium tartrate dibasic, pH 7.0. The post-reaction translocated open structure (+1 Complex, 6UR2), with incorporated dGTP, was obtained after ~45 d by mixing the same protein complex solution 1:1 with 0.8 M sodium succinate, pH 7.0. For all crystals, the space group was P212121, and the structures were solved by molecular replacement.

Primer extension assays. Except where indicated, all extension reactions were performed with 1 μM fluorescein-labeled primer, 1.5 μM template, and ~1.1 μM purified His6-tagged protein at 55° C. in a reaction buffer composed of 40 mM Tris-HCl, pH 8.8, 1 mM DTT, and a divalent cation as specified, typically 10 mM $CaCl_2$. Reaction mixtures were equilibrated at the indicated reaction temperature for 1 min and initiated by addition of substrate. Progress was monitored by sampling 1 μL from the reaction manually quenched into 24 μL of chilled 90% formamide, 10 mM EDTA. Quenched samples were denatured at 90° C. for 1 min and cooled to room temperature prior to separation by denaturing polyacrylamide gel electrophoresis on 20% TBE-urea gels. To maintain strand separation for long extension products, as in FIGS. 3F-3I, an unlabeled DNA oligonucleotide complementary to the template was added to the quenching buffer (~2 μM) prior to denaturation. Typically, 3 or 4 μL of quenched sample was loaded per lane for gels of 0.75-mm thickness. Bands were visualized with a Typhoon laser scanning imager (GE Amersham) and quantified with the manufacturer's software. For acid digestion of extended products, a reaction sample was diluted with 2.5 volumes of 1% acetic acid, 10 mM EDTA in formamide and digested at 75° C. for 45 min prior to gel separation.

Mass spectrometry. Reaction samples were desalted using C18 ZipTips equilibrated with LC-MS grade methanol followed by 2 M triethylammonium acetate, pH 7 (TEAA). The sample was diluted by addition of TEAA buffer to a concentration of 0.2 M and bound to the support. The resin was then washed with at least 100 μL of 20 mM TEAA. The sample was eluted in 50% methanol directly into an HPLC vial insert and dried in a centrifugal vacuum concentrator.

Example 1: Reactant and Product Polymerase "Open" Complexes Containing a 3'-Amino Primer or a N3'→P5' Phosphoramidate Bond It was recently reported that reverse transcriptases can recognize NP-DNA templates and synthesize a complementary DNA strand, suggesting that the structural homology between NP-DNA and native nucleic acids is sufficient to support polymerase activity (Lelyveld et al., DNA polymerase activity on synthetic N3'→P5' phosphoramidate DNA templates. *Nucleic Acids Res.* 47, 8941-8949 (2019)). However, enzymatic synthesis of NP-DNA would require not only recognition of the genetic polymer, but also a novel chemistry at the active site. For such catalysis to occur, the 3'-amino terminal primer would, at a minimum, need to adopt a conformation related to that seen in the native reaction center.

Studies described herein investigate the structural consequences of 3'-amino sugar substitution at the terminus of a primer in an enzymatic context. Crystals of the large fragment of DNA polymerase I (BF) from the thermophilic bacterium *Bacillus stearothermophilus* (Bst, now classified as *Geobacillus*) complexed with a DNA duplex in which the primer contains a terminal 3'-amino-2',3'-dideoxycytidine (nC) residue were grown (FIGS. 1A-1F). The crystal structure of the complex was solved by molecular replacement to a resolution of 2.25 Å (FIGS. 1A-1F and Tables 2-3).

TABLE 2

Crystal X-ray data collection statistics.

| Structure | 1 | 2 | 3 | 4 |
|---|---|---|---|---|
| Space group | $P2_12_12_1$ | $P2_12_12_1$ | $P2_12_12_1$ | $P2_12_12_1$ |
| Unit cell parameters (Å, °) | 85.20, 93.68, 107.14, 90.00, 90.00, 90.00 | 87.61, 93.92, 106.12, 90.00, 90.00, 90.00 | 93.63, 108.07, 149.75, 90.00, 90.00, 90.00 | 93.76, 108.80, 149.97, 90.00, 90.00, 90.00 |
| Resolution range, Å (last shell) | 50-2.27 (2.36-2.27) | 50-2.25 (2.33-2.25) | 50-2.1 (2.18-2.1) | 50-2.25 (2.33-2.25) |
| Unique reflections | 39951 | 40025 | 89397 | 72498 |
| Completeness, % | 99.9 (100) | 94.4 (83.2) | 100 (100) | 98.4 (90.4) |
| $R_{merge}$, % | 12 (50.8) | 14.1 (57.4) | 8.2 (46.2) | 12.5 (60.5) |
| <I/σ(I)> | 17.9 (4.7) | 15.1 (6.8) | 23.4 (3.55) | 10.0 (2.67) |
| Redundancy | 8.0 (8.0) | 7.0 (6.0) | 7.3 (7.3) | 3.6 (3.3) |

TABLE 3

Crystal structure refinement statistics.

| Structure | 1 | 2 | 3 | 4 |
|---|---|---|---|---|
| PDB code | 6UR2 | 6UR4 | 6UR9 | 6US5 |
| Complexes per asymmetric unit | 1 | 1 | 2 | 2 |
| Resolution range, Å | 40.85-2.27 | 28.4-2.25 | 46.8-2.1 | 47.1-2.25 |
| $R_{work}$, % | 22.9 | 20.5 | 20.4 | 22.4 |
| $R_{free}$, % | 27.7 | 24.4 | 24.3 | 27.8 |
| Number of reflections | 37883 | 40004 | 89393 | 72436 |
| Bond length R.M.S. (Å) | 0.008 | 0.013 | 0.031 | 0.055 |
| Bond angle R.M.S. | 1.55 | 1.818 | 6.642 | 7.639 |
| Average B-factors, (Å$^2$) | 42.6 | 30.1 | 42.4 | 50.8 |

Figure 1A:
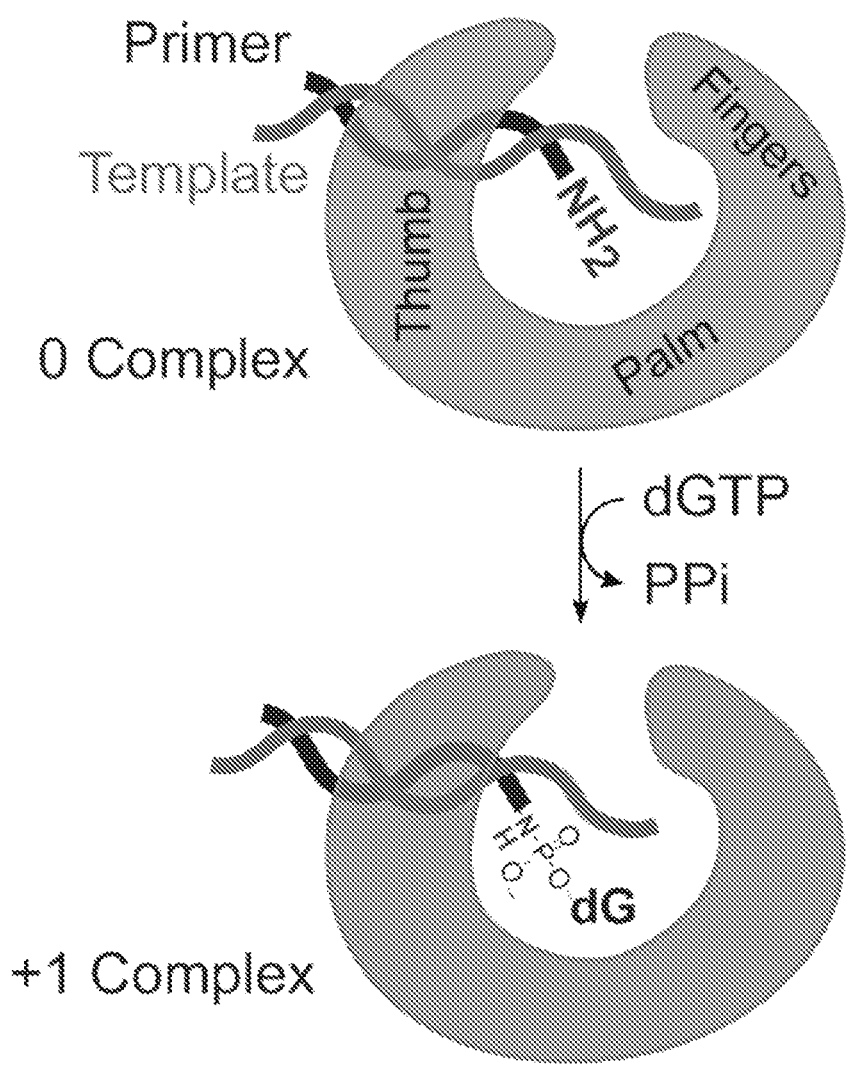
FIG. 1A shows a cartoon of ternary complexes. The "0 complex" contains wild-type DNA polymerase I (BF) from the thermophilic bacterium *Bacillus stearothermophilus*, 3'-amino terminal DNA primer (5'-GCGATCAGnC (SEQ ID NO:2), black), and DNA template (5'-ACACGCT-GATCGCA (SEQ ID NO:3), gray) in an open conformation. The "+1 complex" formed by in-situ primer extension with dGTP, forming a phosphoramidate linkage, followed by translocation.
Figure 1B:
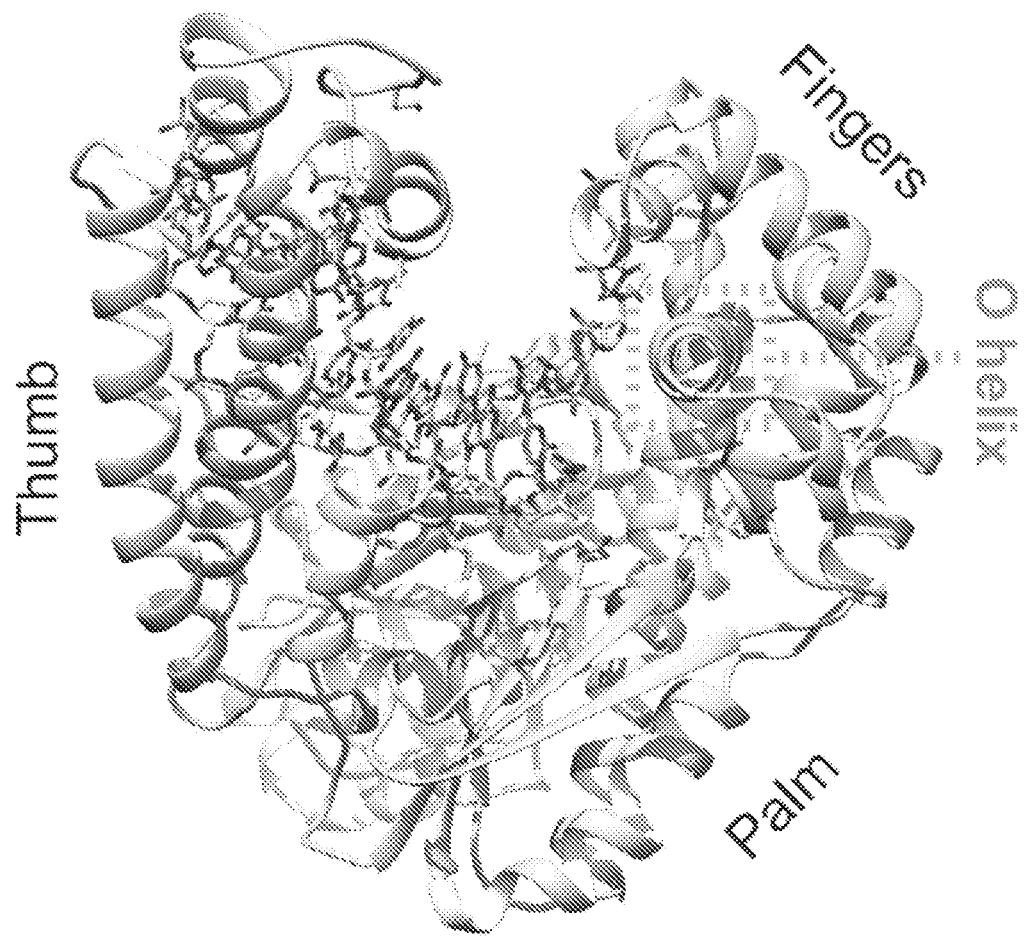
FIG. 1B shows the 0 complex structure solved at 2.25 Å. BF is ribbon cartooned, bound to unextended primer/template in the open conformation (PDB 6UR4).
Figure 1C:
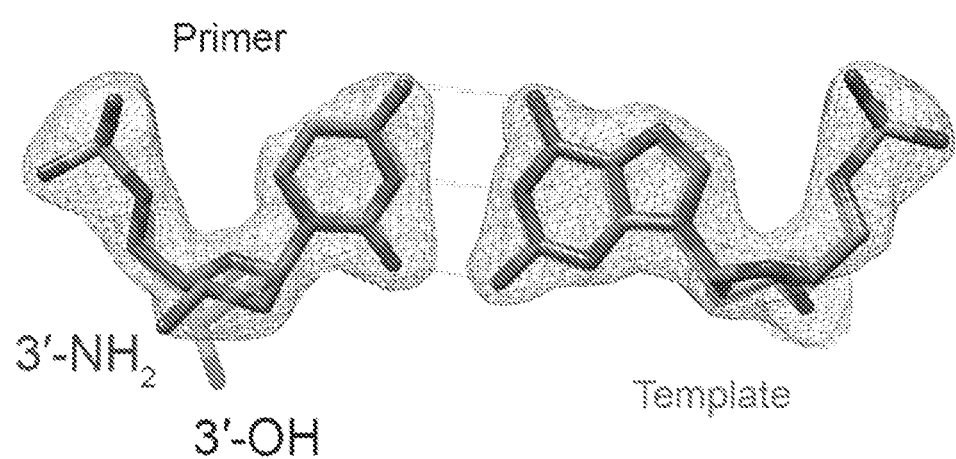
FIG. 1C shows an overlay of the 3'-terminal nC sugar in the 0 complex (gray bonds) and that of a dC terminated primer (gray, PDB 1L5U) (Johnson et al., Processive DNA synthesis observed in a polymerase crystal suggests a mechanism for the prevention of frameshift mutations. *Proc. Natl. Acad. Sci.* 100, 3895-3900 (2003)), as well as the 2Fo-Fc density map (gray mesh, 2 σ) associated with the terminal nC:dG base pair.
Figure 1D:
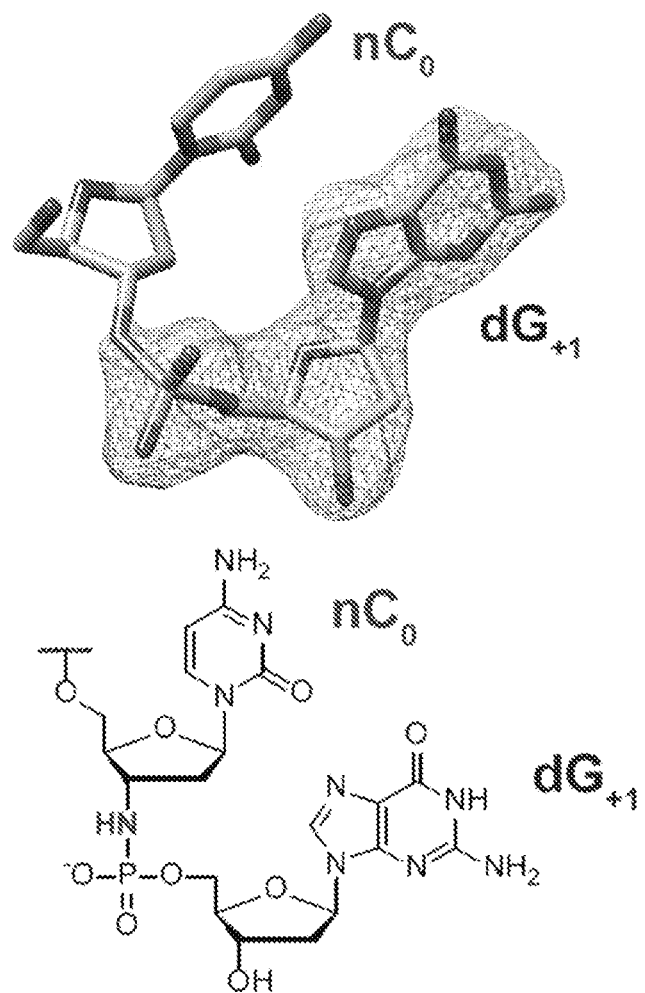
FIG. 1D shows a structure and omit map (top, gray mesh, 4 σ) for the terminal dG (+1) residue extended in situ from the 3'-nC (0) terminated primer in the +1 complex and chemical structure as refined (bottom).
Figure 1E:
FIG. 1E shows the +1 complex structure solved at 2.27 Å in an open post-translocated conformation with +1 extended primer and template (PDB 6UR2).

The enzyme was found in a 1:1 stoichiometry with the bound duplex in the asymmetric unit, with the nC terminated primer aligned at the canonical phosphodiester bond-forming active site (FIG. 1A, 0 Complex). Although the crystal was grown in the presence of free 2'-deoxyguanosine 5'-triphosphate (dGTP) and $Mg^{2+}$, no ordered metal ion or nucleotide was apparent. The structure is consistent with an "open" conformation (Kiefer et al., Visualizing DNA replication in a catalytically active *Bacillus* DNA polymerase crystal. *Nature* 391, 304-307 (1998)), in which the "O-helix" of the fingers domain (698-714) is arrayed distally from the primer terminus, allowing significant solvent access to the reaction center (FIG. 1B). Density for the 3'-amino-2',3'-dideoxyribose sugar of the terminal nC residue was consistent with a C3'-endo conformation, in concordance with the A-form geometry seen in crystallographic and NMR studies of NP-DNA duplexes (Ding et al., An Oligodeoxyribonucleotide N3'→P5' Phosphoramidate Duplex Forms an A-type Helix in Solution. *Nucleic Acids Res.* 24, 354-360 (1996); Ding et al., NMR Solution Structure of the N3'→P5' Phosphoramidate Duplex d(CGCGAATTCGCG)$_2$ (SEQ ID NO:7) by the Iterative Relaxation Matrix Approach. *Biochemistry* 37, 12082-12093 (1998); and Tereshko et al., Consequences of Replacing the DNA 3'-Oxygen by an Amino Group: High-Resolution Crystal Structure of a Fully Modified N3'→P5' Phosphoramidate DNA Dodecamer Duplex. *J. Am. Chem. Soc.* 120, 269-283 (1998)) (FIG. 1C).

Figure 1F:
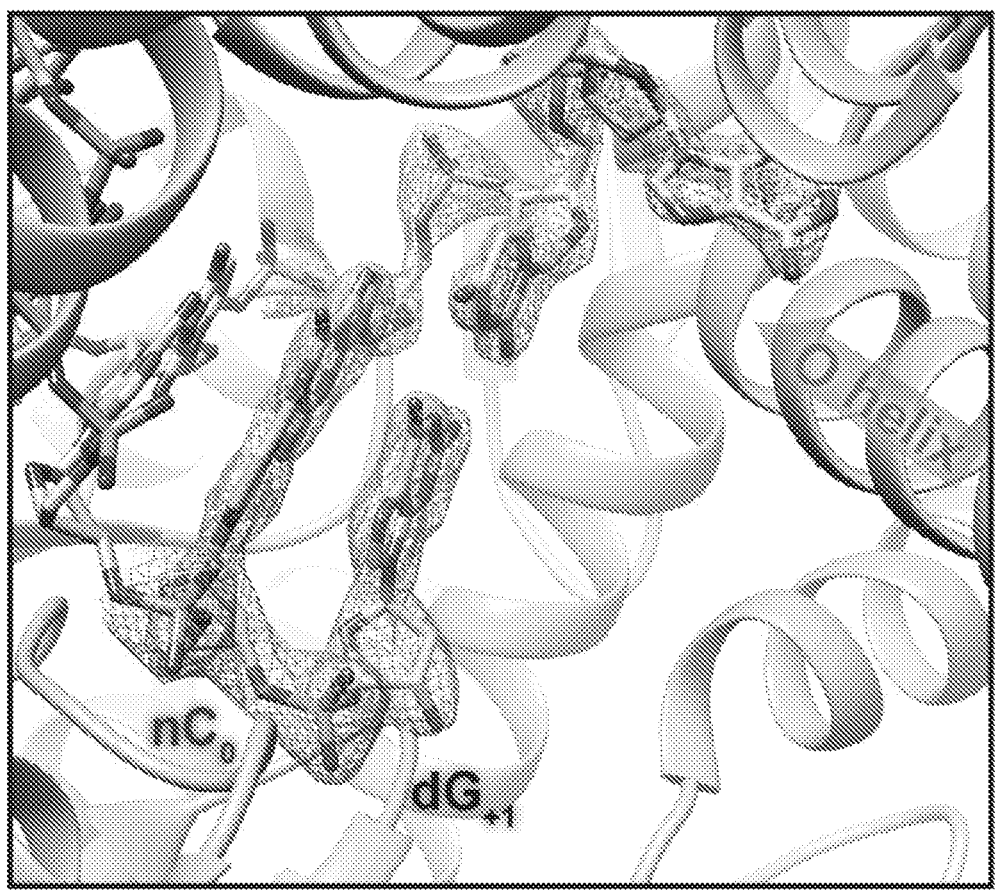
FIG. 1F shows an enlarged view of the +1 complex active site, showing the extended dG residue and associated 2Fo-Fc map overlay (gray mesh, 2 σ).

Under different conditions, a slow-growing crystal emerged after ~45 days, yielding a 2.27-Å structure of an alternative view of the complex. While the solved structure was again consistent with an open conformation, it was found during refinement that the observed density for the bound duplex was best explained as a post-translocation translocated product complex containing a covalently incorporated deoxyguanosine (dG) residue at the +1 position of the primer strand (+1 complex, FIGS. 1D-1F). The density of the added dG is well-defined in the complex, as is the density corresponding to the +2 template deoxyadenosine (dA), now positioned in the proximal templating position in a pocket formed by the O and P helices of the fingers domain (FIG. 1F).

Figure 6:
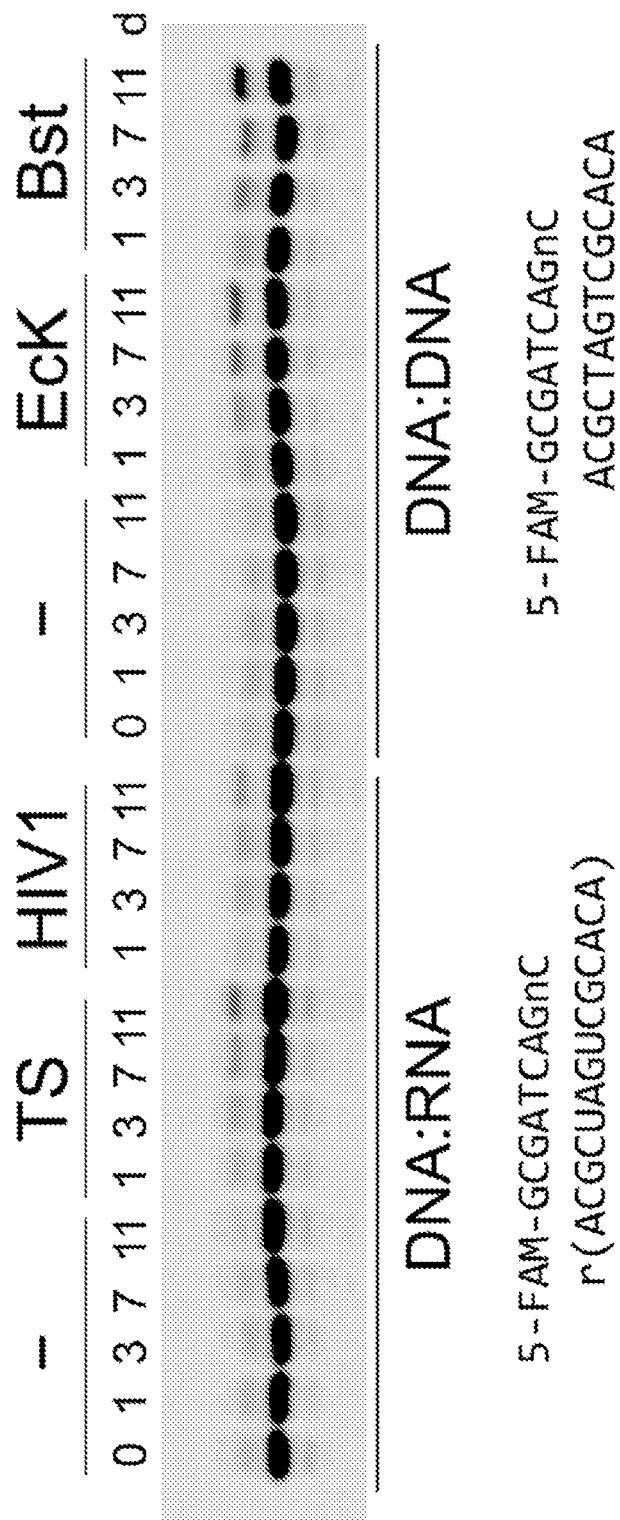
FIG. 6 shows data from 3'-amino terminal primer extension under crystallization conditions. Reactions were carried out with 1 μM of the indicated primer and 1.5 μM of the indicated template at 37° C. in 0.2 M sodium succinate, pH 7.0, with 10 mM dGTP and 10 mM DTT. Samples quenched 1:25 in 90% formamide with 10 mM EDTA were separated on a 24% denaturing polyacrylamide TBE-urea gel and visualized with a laser scanning fluorescence imager. TS, Thermoscript reverse transcriptase (Life Technologies); HIV1, HIV-1 reverse transcriptase (Worthington Biochemical); EcK, *E. coli* Klenow fragment (exo-, New England Biolabs); Bst, Bst DNA polymerase large fragment 3.0 variant (New England Biolabs).
Figure 7A:
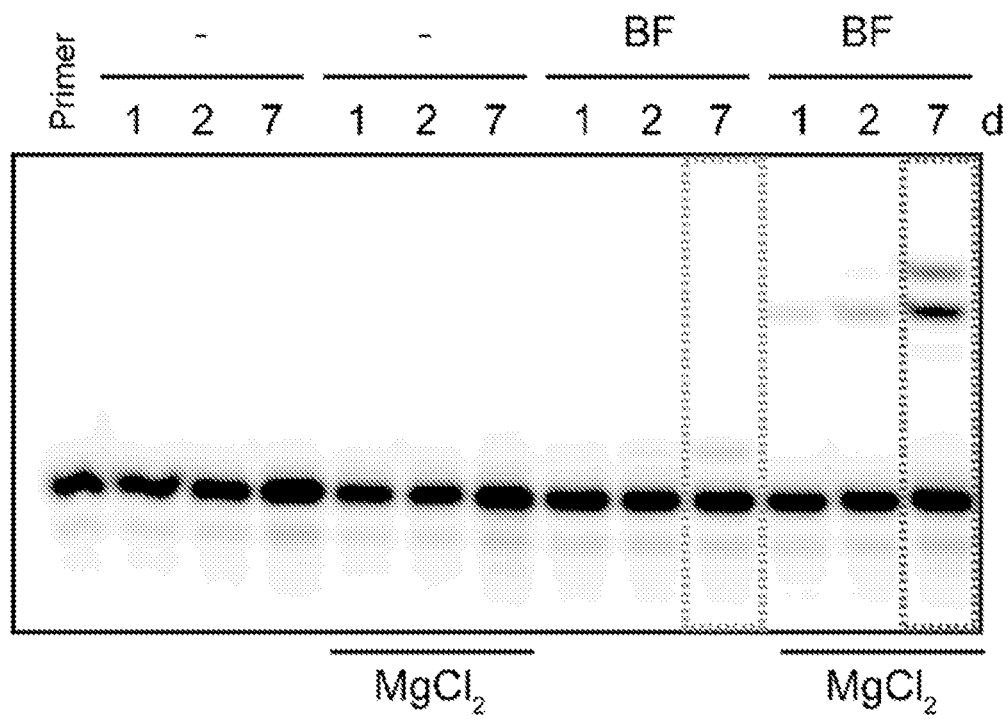
FIG. 7A shows primer extension with the indicated primer (2 μM) and template (2.2 μM) at 37° C. in 0.2 M sodium succinate, pH 7.0, with 10 mM dGTP, 10 mM DTT, and 10 mM $MgCl_2$ where indicated. BF, wild-type Bst DNA polymerase large fragment.
Figure 7B:
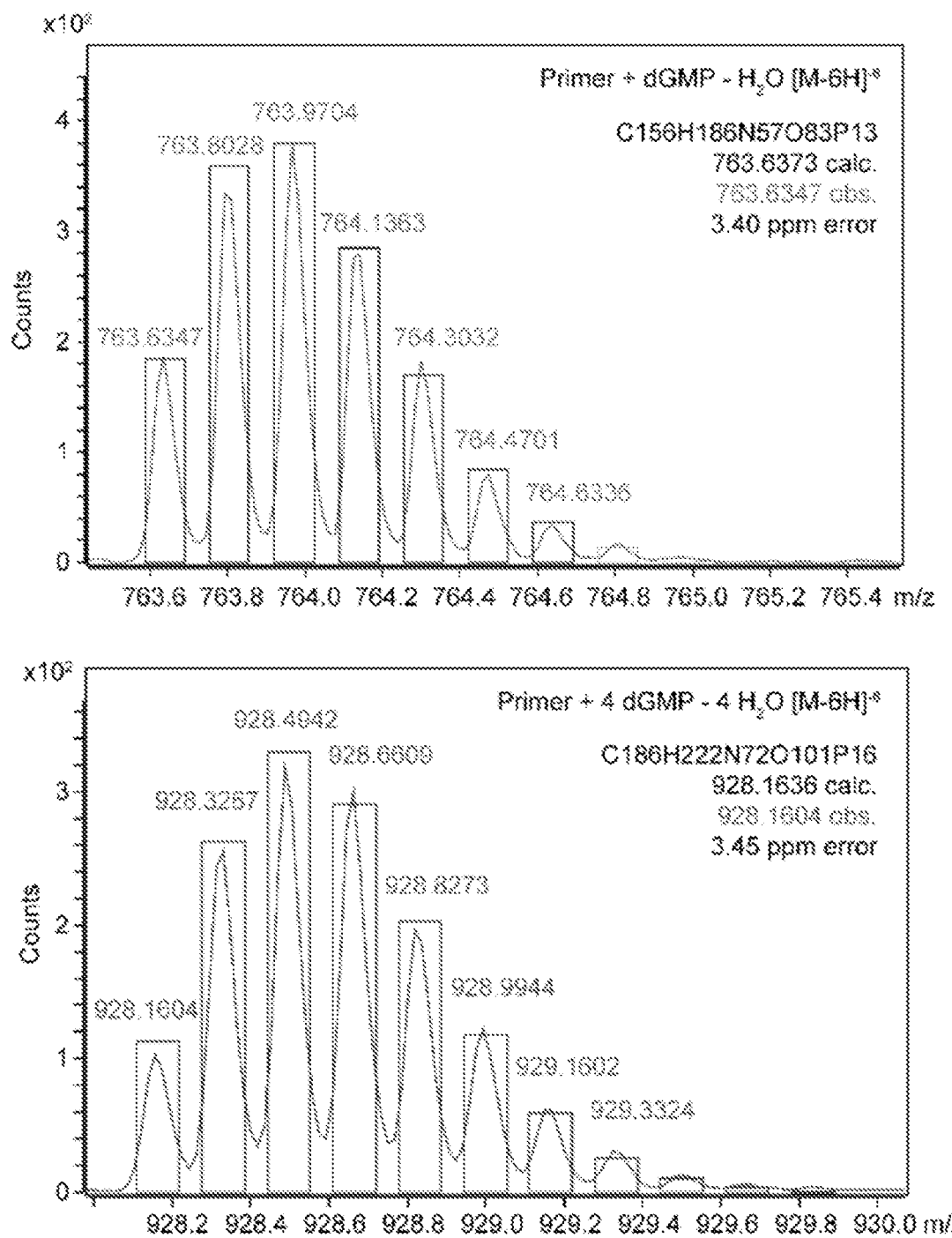
FIG. 7B shows high resolution mass spectra of extended NP-bonded extended products observed as the $[M-6H]^{6-}$ ions detected in samples of BF reactions with (gray, top) or without (gray, bottom) the addition of Mg', prepared from the same samples as in lanes indicated in FIG. 7A with dashed boxes of the corresponding color. Predicted isotope distribution for the indicated chemical formulas overlaid in red boxes.

A primer extension reaction occurring on a timescale of weeks could reflect a background uncatalyzed rate or a process that occurs solely in crystallo. It was therefore sought to establish whether NP bond formation occurs in solution and, if so, whether this reaction is in fact catalyzed by the polymerase. When incubated under conditions similar to the mother liquor in which extension was first observed crystallographically, slow extension of the 3'-amino primer could be observed in a polymerase-dependent manner on a timescale of days in solution (FIG. 6). By high resolution mass analysis of the reactions, ions consistent with the NP bonded +1 product were detected with 3.4 ppm mass error and corresponding isotopic distribution, while no products of 3'-5' exonucleolytic activity and/or extension were detected (FIG. 7A-7B).

Taken together, these results demonstrate that DNA polymerase adopts an "open" conformation to produce a N3'→P5' phosphoramidate bond.

Example 2: Polymerase-Catalyzed 3'-Amino Primer Extension and NP-DNA Synthesis

Figure 2A:
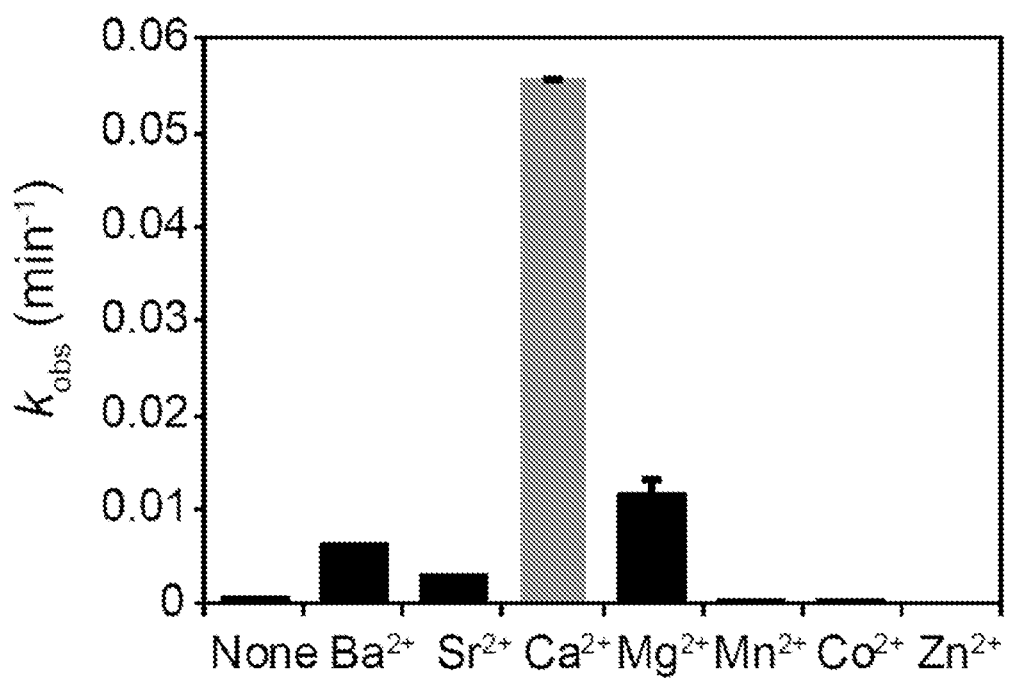
FIG. 2A shows a graph of the effect of divalent metal ion cofactors at 5 mM with 1 µM 3'-amino terminal DNA primer, 1.5 µM DNA template, and 1.1 µM wild-type BF at 55° C. in 40 mM Tris-HCl, pH 8.8, and 1 mM DTT (omitted for $Co^{2+}$). Error bars are s.e.m. for n=2.
Figure 2B:
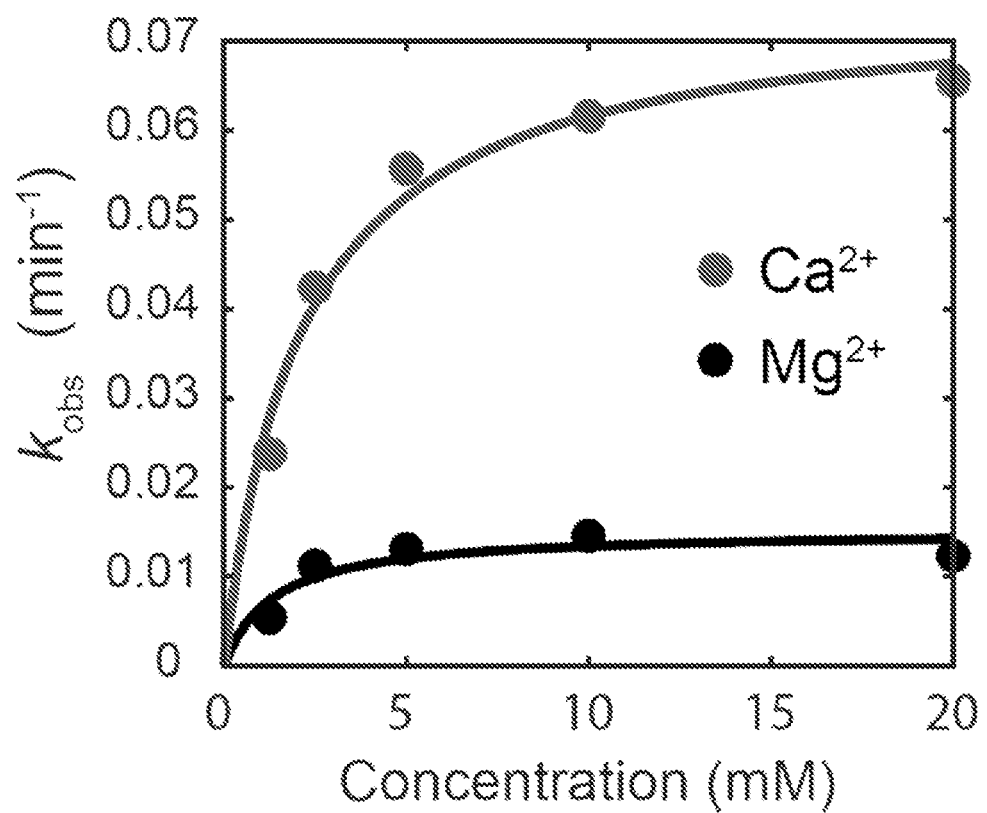
FIG. 2B shows a graph of the observed rate constant, $k_{obs}$, of 3'-amino primer extension by wild-type BF in the presence of 1 mM dCTP and varying concentrations of $CaCl_2$ (gray, $k_{pol}$=0.075 min' and $K_{d,app}$=2.1 mM) or $MgCl_2$ (black, $k_{pol}$=0.015 $min^{-1}$ and $K_{d,app}$=1.3 mM).
Figure 2C:
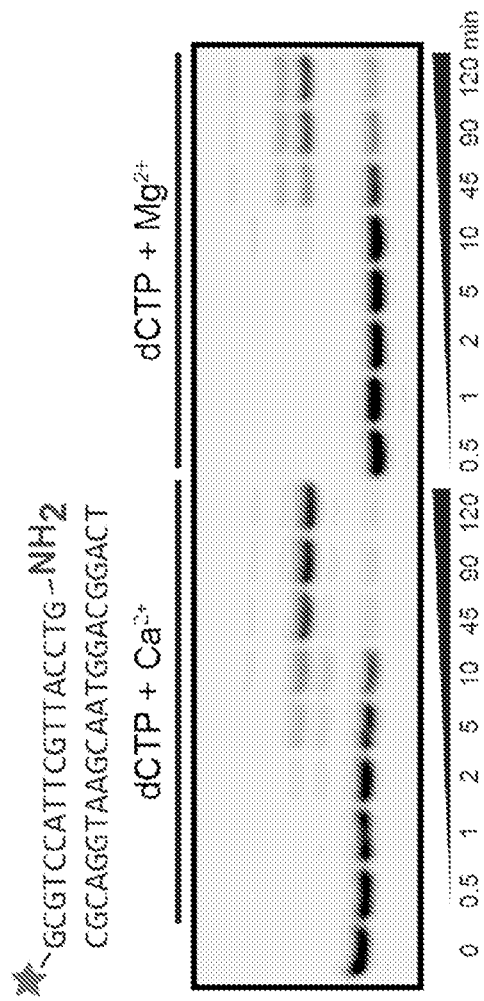
FIG. 2C shows a time course of 3'-amino primer extension reactions (right) with 1 mM dCTP and 10 mM $CaCl_2$ or $MgCl_2$ visualized by denaturing PAGE. Top: fluorescein-labeled 3'-amino terminal primer (GCGTCCATTCGT-TACCTG-$NH_2$; SEQ ID NO: 4) and template DNA duplex (CGCAGGTAAGCAATGGACGGACT; SEQ ID NO: 5) for FIGS. 2A-2C.
Figure 2C:
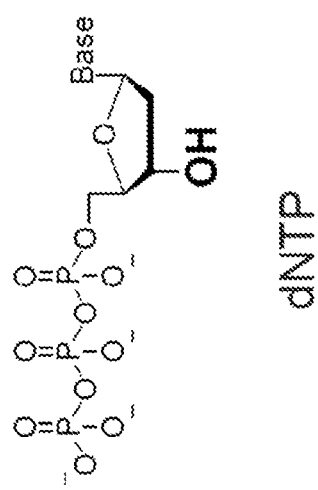

This example reports identification of conditions in which BF is capable of extension beyond a 3'-amino terminus in solution (FIGS. 2A-2D). Divalent metal cofactors were screened under pre-steady-state conditions and strong cofactor-dependent effects on activity were observed. Kinetics of 3'-amino primer extension with 5 mM Ca$^{2+}$, Mg$^{2+}$, Ba$^{2+}$, and Sr$^{2+}$ were all faster than in the absence of added divalent metals (FIG. 2A). The cofactor-dependent kinetics did not follow a trend consistent with the Irving-Williams series nor that expected from the aquo ion pKa. Interestingly, Ca$^{2+}$ had the largest kinetic effect at pH 8.8 and 55° C. When titrated into the reaction, observed rate constants showed saturation behavior at similar apparent dissociation constants, K$_{d,app}$, for Mg$^{2+}$ and Ca$^{2+}$ (1.3 mM vs. 2.1 mM, respectively, in the presence of 1 mM dCTP). However, the maximum reaction velocity was ~5-fold faster in the presence of saturating Ca$^{2+}$ vs. Mg$^{2+}$ (FIGS. 2B-2C), maximally ~4.5 nt/hr with Ca$^{2+}$. Phosphodiester-forming activity with Ca2+ has been reported (Irimia et al., Calcium Is a Cofactor of Polymerization but Inhibits Pyrophosphorolysis by the *Sulfolobus solfataricus* DNA Polymerase Dpo4. *Biochemistry* 45, 5949-5956 (2006); and Ralec et al., Calcium-driven DNA synthesis by a high-fidelity DNA polymerase. *Nucleic Acids Res.* 45, 12425-12440 (2017)). Here, two additions of dCTP were observed on a GG-containing template in the presence of either Ca$^{2+}$ or Mg$^{2+}$, where the first is linked via a phosphoramidate ester and the second via a phosphodiester (FIG. 2C).

Figure 2D:
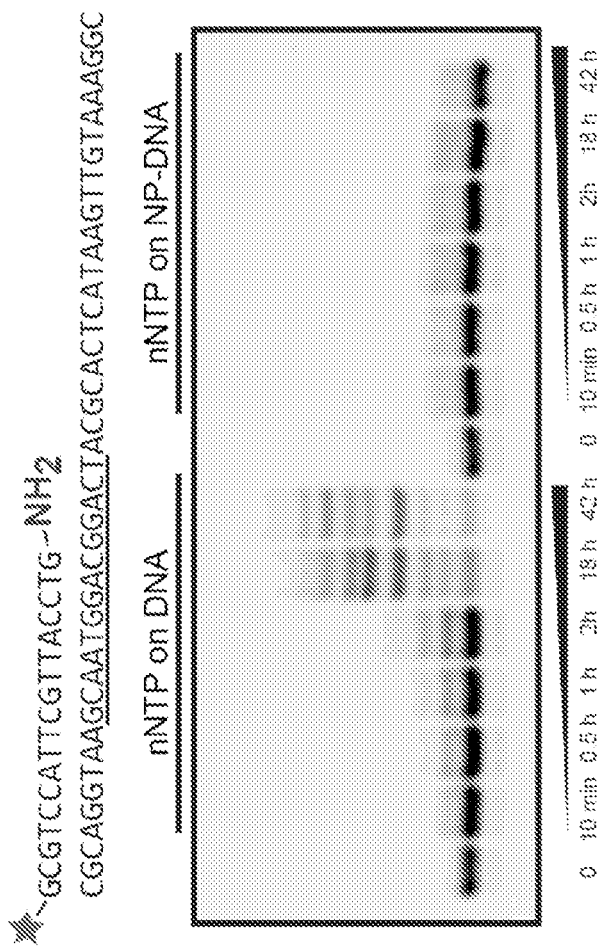
FIG. 2D shows the chemical structure of nNTP substrates (left), and time course of 3'-amino primer extension reactions with 1 mM nNTPs and 10 mM $CaCl_2$) (right). Top: Fluorescein-labeled 3'-amino terminal primer (GCGTC-CATTCGTTACCTG-NH2; SEQ ID NO: 4) and template DNA duplex with underlined region DNA or NP-DNA (CGCAGGTAAGCAATGGACGGACTACGCACT-CATAAGTTGTAAAGGC; SEQ ID NO: 6).
Figure 2D:
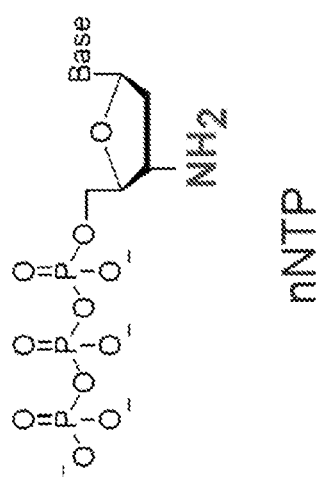

With the enhanced kinetics afforded by Ca$^{2+}$, BF was capable of catalyzing multiple-turnover condensation of nNTP monomers to form NP-DNA oligonucleotides in a DNA template-directed manner (FIG. 2D). Extension up to the +8 nt product was detected after 24 h at 55° C. in the presence of Ca$^{2+}$ and all four nNTP substrates, but no significant extension was observed on an NP-DNA template.

Taken together, these results demonstrate that DNA polymerase forms N3'→P5' phosphoramidate linked oligonucleotides in a template-directed manner.

Figure 3E:
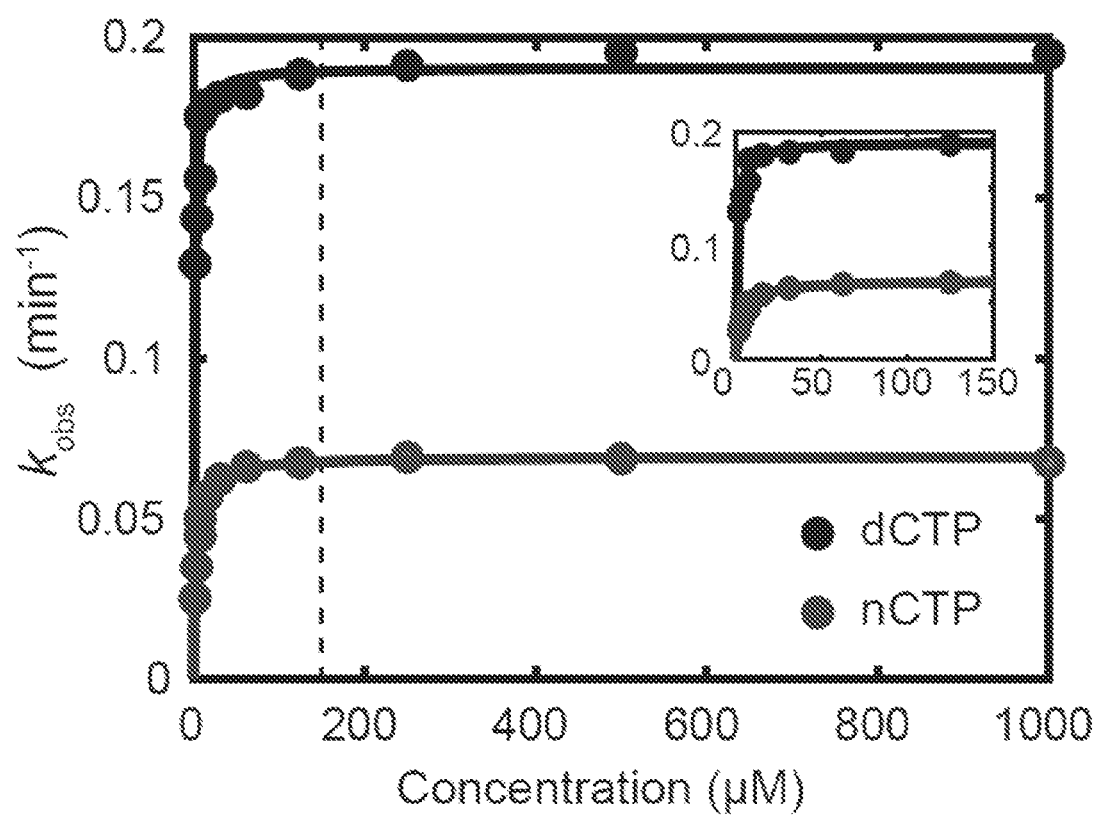
FIG. 3E shows a graph of substrate-dependent rate constants, as in FIG. 3B, for the mutant F710Y (see Table 4).
Figure 3F:
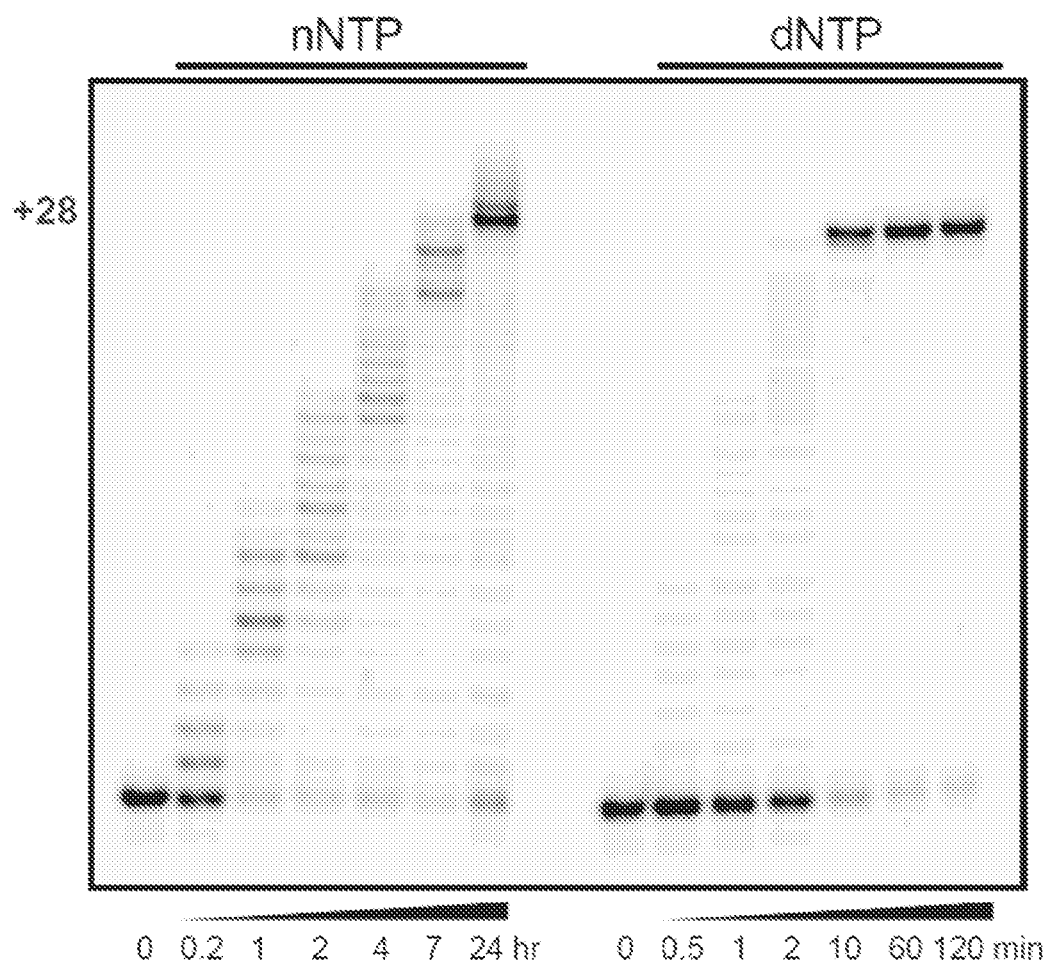
FIG. 3F shows data from a 3'-amino primer extension by mutant F710Y on a mixed sequence template (sequence in FIG. 2D) with either 1 mM nNTPs or dNTPs at 55° C. in a buffer containing 40 mM Tris-HCl, pH 8.8, 10 mM $CaCl_2$), and 1 mM DTT.

Example 3: Substrate-Dependent Kinetic Parameters for NP Activity in DNA Polymerase Although wild-type BF has bona fide DNA-dependent NP-DNA polymerase activity, a substantial kinetic defect is associated with nNTP vs. dNTP addition to a 3'-amino terminal primer (FIG. 3A). For the first addition to a primer ending in nG, the rate constant, k$_{pol}$, in reactions with nCTP was ~22-fold slower than with dCTP (FIG. 3B and Table 4). In seeking to rationalize this apparent recognition of the 3'-substituent, it was first considered that 3'-amino-2',3'-dideoxyribonucleosides adopt a C3'-endo sugar conformation and, as such, bear greater conformational similarity to ribonucleosides than deoxyribonucleosides. It is therefore conceivable that nNTPs might be disfavored based on discrimination of their RNA-like sugar pucker. Selectivity against ribonucleotides purportedly involves recognition by "steric gate" residues, and mutations at these positions alter selectivity against ribonucleotide incorporation (C. M. Joyce, Choosing the right sugar: How polymerases select a nucleotide substrate. *Proc. Natl. Acad. Sci.* 94, 1619-1622 (1997); and Brown and Suo, Unlocking the Sugar "Steric Gate" of DNA Polymerases. *Biochemistry* 50, 1135-1142 (2011)). However, nNTPs and dNTPs are both chemically 2'-deoxy, despite their distinct sugar pseudorotation. Limited screening of mutations at "steric-gate" hotspot positions (FIG. 3C), as well as two highly conserved residues involved in metal cofactor binding, mainly exacerbated selectivity against nCTP (FIG. 3D). However, mutation at one position in the O helix, Phe-710, known to affect substrate preference for 2',3'-dideoxyribonucleotide 5'-triphosphates (ddNTPs) (Tabor and Richardson, A single residue in DNA polymerases of the *Escherichia coli* DNA polymerase I family is critical for distinguishing between deoxy- and dideoxyribonucleotides. *Proc. Natl. Acad. Sci.* 92, 6339-6343 (1995); Astatke et al., How *E. coli* DNA polymerase I (klenow fragment) distinguishes between deoxy- and dideoxynucleotides. *J. Mol. Biol.* 278, 147-165 (1998); and Warren et al., The structural basis for the mutagenicity of 0(6)-methyl-guanine lesions. *Proc. Natl. Acad. Sci.* 103, 19701-19706 (2006)), showed a significant kinetic enhancement, as well as a large effect on dCTP vs. nCTP selectivity. The mutant F710Y demonstrated a 21-fold increase in k$_{pol}$ for nCTP, as well as a 2.6-fold increase for dCTP (FIG. 3E and Table 4). This mutant could achieve extension to a full length +28 nt NP-DNA product in <24 hours at 55° C. in the presence of Ca$^{2+}$ and all four nNTPs (FIG. 3F).

TABLE 4

Substrate-dependent kinetic parameters for NP activity
in BF under pre-steady-state conditions, as in FIG. 3.

|  | $k_{pol}$ | | $K_{d, app}$ | | |
| --- | --- | --- | --- | --- | --- |
|  | dCTP | nCTP | dCTP | nCTP | Selectivity[a] |
|  | min$^{-1}$ | | µM | | dCTP/nCTP |
| WT | 0.075 | 0.0033 | 1.7 | 3.8 | 51 |
| F710Y | 0.191 | 0.069 | 1.1 | 3.6 | 9 |

[a]Selectivity defined as the ratio $(k_{pol}/K_{d, app})_{dCTP}/(k_{pol}/K_{d, app})_{nCTP}$.

Figure 3G:
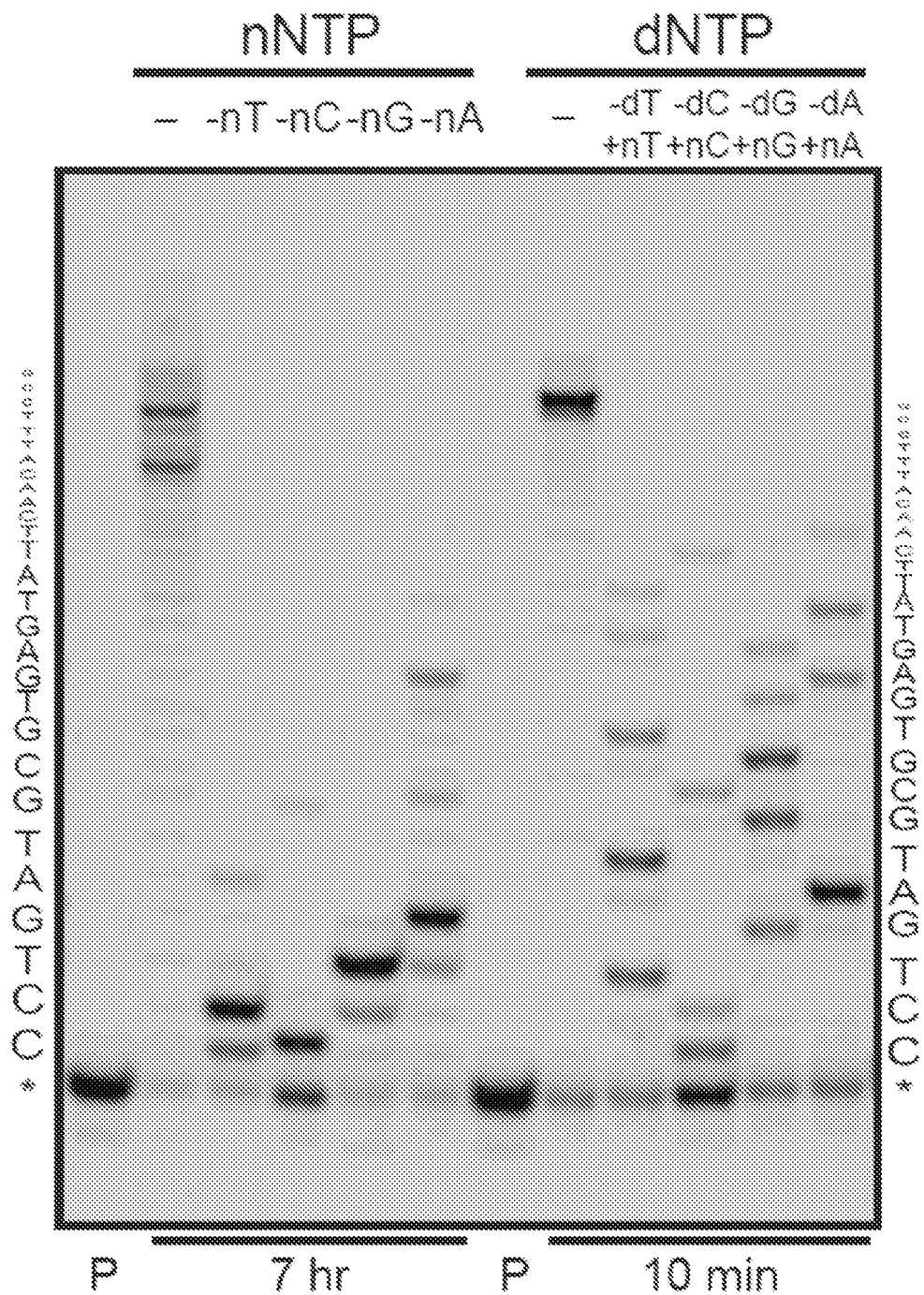
FIG. 3G shows data from extension reactions as in FIG. 3F with nNTP drop-out mixes (left: 0.5 mM each nNTP or only three of four, as indicated) or dNTP drop-in mixes (right: 0.5 mM each dNTP or only three of four, as indicated, with fourth complemented by with the corresponding nNTP). The gel shows reactions incubated for either 7 hr (lanes 2-6) with nNTP drop-out mixes or 10 min (lanes 8-12) with dNTP drop-in mixes. "P" indicates lanes containing primer alone.
Figure 3H:
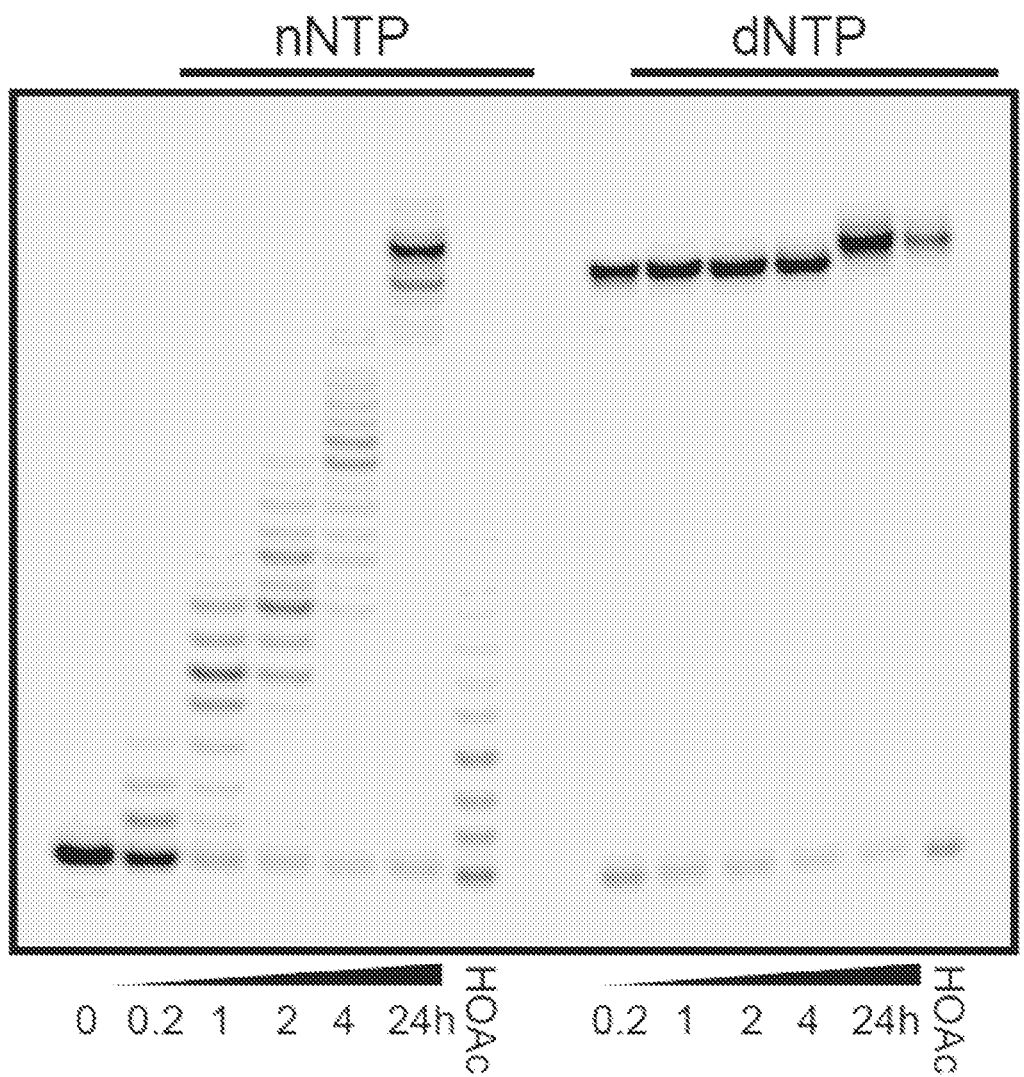
FIG. 3H shows data from a 3'-amino primer extension reactions with F710Y as in FIG. 3F, but showing acid digest products after 24 hr of extension (HOAc lanes).

To establish that NP-DNA polymerase activity is in fact template-directed by BF, sequence specific stalling of primer extension in the presence or absence of individual nucleotides was analyzed. By using drop-out mixes, in which one of the four nNTPs is absent in each reaction, a substantial kinetic block at (or proximal to) the position corresponding to the absent substrate was observed (FIG. 3G, left). With drop-in mixes, in which one nucleotide of a dNTP mix is substituted with its corresponding 3'-amino analog in each reaction, BF generates a Sanger-type ladder, with accumulation of products at positions corresponding to the nNTP present in each reaction (FIG. 3G, right). Finally, the products of these long extension reactions show the acid lability characteristic of NP bonds (FIG. 3I). Incubation of the quenched reaction with acetic acid (HOAc) at 75° C. generated a cleavage ladder for all positions when nNTPs were used for 3'-amino primer extension, whereas no hydrolysis intermediates are observed when dNTPs have been used to extend the same primer.

Relative to its native phosphodiester bond forming activity, the kinetic disadvantage of BF's NP-DNA polymerase activity is approximately four orders-of-magnitude with F710Y, since transient $k_{pol}/K_d$ is 3.1 µM$^{-1}$ s$^{-1}$ vs. 3.2×10$^{-4}$ µM$^{-1}$ s$^{-1}$ for DNA synthesis with Mg$^{2+}$ (Wang et al., Structural factors that determine selectivity of a high fidelity DNA polymerase for deoxy-, dideoxy-, and ribonucleotides. *J. Biol. Chem.* 287, 28215-28226 (2012)) vs. 3.2×10$^{-4}$ µM$^{-1}$ s$^{-1}$ for NP-DNA synthesis with Ca$^{2+}$ (Table 4). This difference is of a similar order to that seen for mismatch incorporation. Unlike mismatches, the binding affinity for cognate nNTPs remains high, and the difference in catalytic efficiency is likely to arise mainly in the chemical step of the reaction. It may nevertheless be instructive to establish whether there are unique structural determinants associated with formation of the phosphoramidate catalytic complex.

Example 4: Structural Snapshots of the Reaction Pathway in NP Catalysis

Figure 4D:
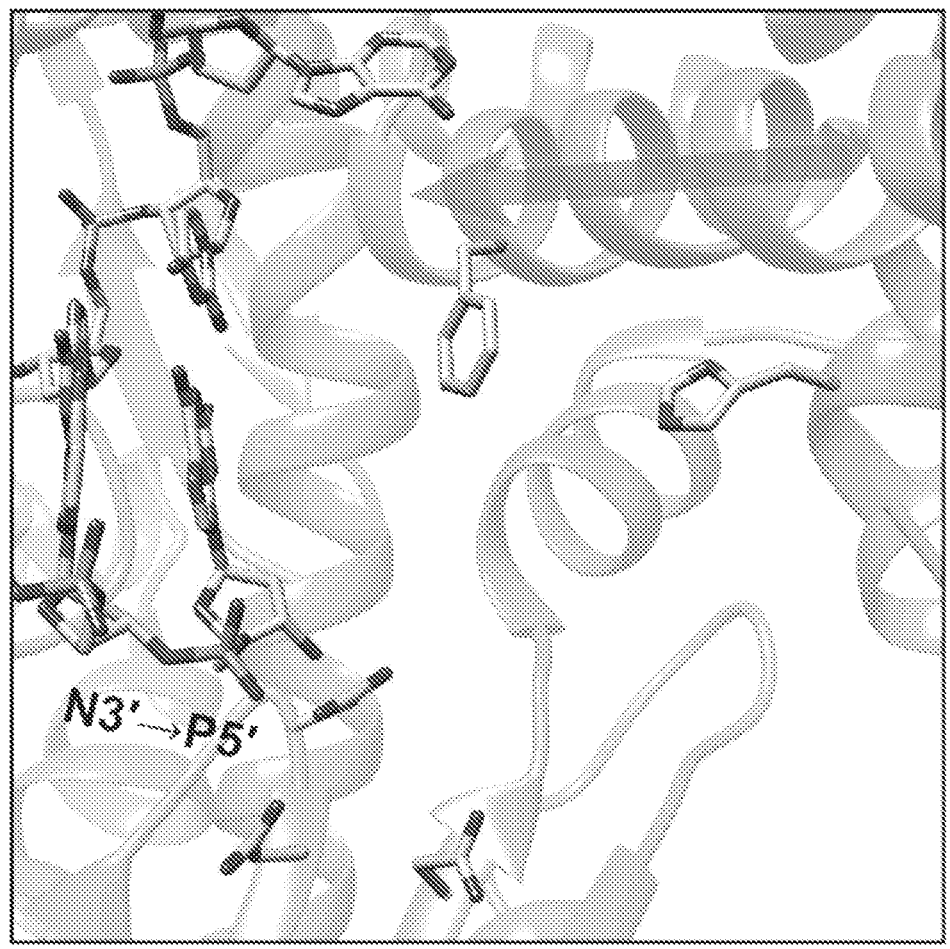
FIG. 4D shows the post-translocated product "+1 complex" in the open conformation, containing an incorporated N3'→P5' bond between the primer terminal nC and dG residues, as in FIGS. 1D-1F (PDB 6UR2). Atomic distances are indicated in Å, and the orientation of the O helix in each structure is shown with a gray arrow.

To observe the major steps in the reaction pathway for NP-DNA synthesis, from the reactant complex (FIG. 1B and FIG. 4A) to the +1 product complex (FIGS. 1E-1F and FIG. 4D), BF was co-crystallized with an unreactive nucleotide analog (dGpNHpp), a 3'-amino terminated DNA primer, and a DNA template. Using the double mutant F710Y/D598A (Warren et al., The structural basis for the mutagenicity of O(6)-methyl-guanine lesions. *Proc. Natl. Acad. Sci.* 103, 19701-19706 (2006), Johnson et al., Processive DNA synthesis observed in a polymerase crystal suggests a mechanism for the prevention of frameshift mutations. *Proc. Natl. Acad. Sci.* 100, 3895-3900 (2003)), the analog-bound complex with Mn$^{2+}$ was crystallized and the structure was solved to 2.25 Å resolution (FIG. 4B).

Two complexes were found in the asymmetric unit, both substrate bound in a closed conformation of the fingers domain, as seen by a large conformational change in the O helix proximal to the reaction center. A single metal ion was coordinated by the α,β-imido-triphosphate moiety in each active site, although the bound metal ion and substrate is more ordered in one of the two complexes in the asymmetric unit. In this complex, the terminal 3'-amino group of the primer is in close proximity with the alpha-phosphorus of the analog (N3'-P$_\alpha$ distance ~3.8 Å), as well as with the carboxylate group of Asp-830 in the active site (N3'-O distance ~2.3 Å, FIG. 4C), significantly closer than the ~2.9-3.0 Å seen in the open conformation (FIG. 4A). This highly conserved aspartate coordinates divalent metal ions in structures of the equivalent native complex when the primer bears a 3'-OH, but there is substantial debate over its potential role as a general base in native phosphodiester catalysis (Castro et al., Two proton transfers in the transition state for nucleotidyl transfer catalyzed by RNA- and DNA-dependent RNA and DNA polymerases. *Proc. Natl. Acad. Sci.* 104, 4267-4272 (2007); Steitz et al., A unified polymerase mechanism for nonhomologous DNA and RNA polymerases—Comment/reply. *Sci. Wash.* 266, 2022 (1994); and Pelletier et al., Structures of ternary complexes of rat DNA polymerase beta, a DNA template-primer, and ddCTP. *Science* 264, 1891-1903 (1994)). In the closed substrate-bound structure, the aspartate conformation is not significantly altered as a result of 3'-amino substitution at the primer terminus relative to that seen previously with 2',3'-dideoxy termini (Johnson et al., Processive DNA synthesis observed in a polymerase crystal suggests a mechanism for the prevention of frameshift mutations. *Proc. Natl. Acad. Sci.* 100, 3895-3900 (2003)). Nevertheless, this carboxylate appears to be critical, as the mutation D830N entirely abolishes NP-DNA synthesis (FIG. 3D). On the other hand, the mutation E831Q did not substantially affect activity, although this adjacent residue is typically found coordinating a metal ion in structures modeling the native DNA polymerase activity. In the analogous nonenzymatic chemistry with phosphorimidazolides, rapid kinetics are observed in the absence of divalent metal ions, suggesting that inner sphere metal coordination is superfluous for the reactivity of the 3'-amino nucleophile (Zhang et al., Synthesis of N3'-P5'-linked Phosphoramidate DNA by Nonenzymatic Template-Directed Primer Extension. *J. Am. Chem. Soc.* 135, 924-932 (2013); Zhang et al., Fast and accurate nonenzymatic copying of an RNA-like synthetic genetic polymer. *Proc. Natl. Acad. Sci.* 110, 17732-17737 (2013); and Röthlingshöfer and Richert, Chemical Primer Extension at Submillimolar Concentration of Deoxynucleotides. *J. Org. Chem.* 75, 3945-3952 (2010)).

An alternative model of the catalytic complex was produced by co-crystallization with nGTP and a template-bound primer carrying a 3'-terminal 2',3'-dideoxycytidine (ddC) residue. This complex with the BF double-mutant was crystallized and solved to 2.10 Å resolution (FIG. 4C). The resulting structure shows a single ordered Ca$^{2+}$ and substrate in the closed conformation, but only in one of two complexes in the asymmetric unit (FIG. 5A). In the closed complex, a possible role for the mutation F710Y is suggested by the orientation of the tyrosine hydroxyl, which is in close proximity to both the β-phosphate non-bridging oxygen of the incoming substrate and its 3'-amino group. This position is similar to that seen in the presence of a dideoxynucleotide substrate (Warren et al., The structural basis for the mutagenicity of O(6)-methyl-guanine lesions. *Proc. Natl. Acad. Sci.* 103, 19701-19706 (2006)). The noncovalent bonding network also appears to involve the heterocyclic nitrogen of His-682 (FIGS. 4B-4C). Moderate donor-acceptor distances across this network, 2.6-2.8 Å, suggest a distributed hydrogen-bonding stabilization of the substrate and leaving group (FIG. 5A). In the dGpNHpp analog-bound reaction complex, the C2'-endo sugar conformation of the substrate analog is such that a solvent water is bound within this network (FIG. 4B), whereas the 3'-amino group of nGTP in the C3'-endo conformation appears to substitute for this water in the alternative closed complex (FIG. 4C). However, the apparent binding affinity for nCTP vs. dCTP was unaffected by F710Y with $Ca^{2+}$, indicating that this tuning of the substrate is likely relevant only to its conformation in the closed catalytic complex.

Other Embodiments

All of the features disclosed in this specification can be combined in any combination. Each feature disclosed in this specification can be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments can be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases can encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for producing an oligonucleotide comprising phosphoramidate-linked nucleotides, the method comprising:
incubating a sample comprising a DNA polymerase variant comprising an amino acid sequence that is at least 90% identical to SEQ ID NO: 1, wherein the amino acid sequence comprises an amino acid substitution at position F710 which is F710Y; a divalent metal ion cofactor; 3'-amino-2',3'-dideoxyribonucleotide 5'-triphosphates (nNTPs); a 3'-amino terminated primer; and a DNA template comprising, from 3' to 5', a sequence complementary to the primer and a nucleic acid sequence of interest; under conditions and for a time sufficient for the DNA polymerase variant to produce the oligonucleotide comprising phosphoramidate-linked nucleotides, wherein the DNA polymerase variant catalyzes template-directed addition of nNTPs to the primer via formation of N3'→P5' phosphoramidate bonds.

2. The method of claim 1, wherein the amino acid sequence is at least 95% identical to SEQ ID NO: 1.

3. The method of claim 1, wherein the DNA polymerase variant comprises the amino acid sequence set forth in SEQ ID NO: 1.

4. The method of claim 1, wherein the DNA polymerase variant is prepared from cells that express the DNA polymerase variant.

5. The method of claim 1, wherein the DNA polymerase variant is in a cell lysate from cells that express the DNA polymerase variant.

6. The method of claim 1, wherein the sample is incubated at a temperature of 50 to 65° C.

7. The method of claim 1, wherein the sample is incubated for 1 to 24 hours.

8. The method of claim 1, wherein the sample is incubated at a pH of 7 to 10.

9. The method of claim 1, wherein the divalent metal ion cofactor is selected from the group consisting of $Ba^{2+}$, $Sr^{2+}$, $Ca^{2+}$, $Mg^{2+}$, $Mn^{2+}$, $Co^{2+}$, and $Zn^{2+}$.

10. The method of claim 1, wherein the nNTPs comprise nATP, nGTP, nCTP, and/or nTTP.

11. The method of claim 1, wherein the 3'-amino terminated primer comprises ribonucleotides and/or deoxyribonucleotides.

12. The method of claim 1, wherein the 3'-amino terminated primer comprises a 3'-amino terminal ribonucleotide selected from the group consisting of 3'-amino-adenosine, 3'-amino-guanosine, 3'-amino-cytidine, and 3'-amino-uridine.

13. The method of claim 1, wherein the 3'-amino terminated primer comprises a 3'-amino terminal dideoxynucleotide selected from the group consisting of 3'-amino-2',3'-dideoxyadenosine (nA), 3'-amino-2',3'-dideoxythymidine (nT), 3'-amino-2',3'-dideoxycytidine (nC), and 3'-amino-2',3'-dideoxyguanosine (nG).

14. The method of claim 1, wherein the 3'-amino terminated primer comprises a label.

15. The method of claim 1, wherein the 3'-amino terminated primer comprises phosphodiester-linked nucleotides and/or phosphoramidate-linked nucleotides.

16. The method of claim 1, wherein the 3'-amino terminated primer is 5 to 200 nucleotides in length.

17. The method of claim 1, wherein the 3'-amino terminated primer comprises at least 5 or at least 25 consecutive phosphoramidate-linked nucleotides.

18. The method of claim 1, wherein each nucleotide in the 3'-amino terminated primer is phosphoramidate-linked.

19. The method of claim 1, wherein the oligonucleotide is 25 to 250 nucleotides in length.

20. The method of claim 1, wherein the oligonucleotide comprises phosphoramidate-linked nucleotides and phosphodiester-linked nucleotides.

21. The method of claim 1, wherein the oligonucleotide comprises at least 25, at least 50, or at least 100 consecutive phosphoramidate-linked nucleotides.

22. The method of claim 1, wherein each nucleotide in the oligonucleotide is phosphoramidate-linked.

23. The method of claim 1, wherein the sample further comprises nucleoside triphosphates (NTPs).

24. The method of claim 23, wherein the NTPs comprise deoxynucleoside triphosphates (dNTPs).

\* \* \* \* \*